(12) United States Patent
Albarracín Cárdenas et al.

(10) Patent No.: US 11,753,439 B2
(45) Date of Patent: Sep. 12, 2023

(54) *GIARDIA* RECOMBINANT ANTIGENS, PURIFICATION OF POLYCLONAL ANTI-*GIARDIA* IGG AND IGY ANTIBODIES AND *GIARDIA* DETECTION

(71) Applicant: INSTITUTO NACIONAL DE SALUD, Bogota (CO)

(72) Inventors: Ángela Liliana Albarracín Cárdenas, Bogotá (CO); Adriana Arévalo Jamaica, Bogotá (CO); Sofía Duque Beltrán, Bogotá (CO); Fabio Leonardo Quintero Vargas, Bogotá (CO); Cesar Augusto Ramírez Segura, Bogotá (CO)

(73) Assignee: Instituto Nacional de Salud, Bogotá (CO)

( * ) Notice: Subject to any disclaimer, the term of this patent is extended or adjusted under 35 U.S.C. 154(b) by 623 days.

(21) Appl. No.: 16/619,719

(22) PCT Filed: Dec. 18, 2017

(86) PCT No.: PCT/IB2017/058083
§ 371 (c)(1),
(2) Date: Jan. 24, 2020

(87) PCT Pub. No.: WO2019/021049
PCT Pub. Date: Jan. 31, 2019

(65) Prior Publication Data
US 2020/0354401 A1 Nov. 12, 2020

(30) Foreign Application Priority Data
Jul. 25, 2017 (CO) .......... NC2017/0007377

(51) Int. Cl.
*C07K 1/22* (2006.01)
*C07K 16/02* (2006.01)
*G01N 33/569* (2006.01)

(52) U.S. Cl.
CPC ............... *C07K 1/22* (2013.01); *C07K 16/02* (2013.01); *G01N 33/569* (2013.01)

(58) Field of Classification Search
CPC .......... C07K 16/02; C07K 1/22; C07K 16/20; G01N 33/56905; G01N 33/569; A61K 39/00
See application file for complete search history.

(56) References Cited

U.S. PATENT DOCUMENTS

2003/0064417 A1  4/2003  Buechler et al.
2015/0118264 A1  4/2015  Baumhof et al.

FOREIGN PATENT DOCUMENTS

EP  0390460 A2  10/1990

OTHER PUBLICATIONS

Castillo-Romero et al., (PLoS Negl Trap Dis. Jun. 1, 2010;4(6):e697) (Year: 2010).*

(Continued)

*Primary Examiner* — Jana A Hines
(74) *Attorney, Agent, or Firm* — The Morales Law Firm; Joseph L. Morales, Esq.

(57) ABSTRACT

The present invention relates to a stationary phase for the purification of polyclonal anti-*Giardia* IgG and IgY antibodies, as well as a method for purifying polyclonal anti-*Giardia* IgG and IgY antibodies by affinity chromatography. The invention also relates to the polyclonal anti-*Giardia* IgG and IgY antibodies purified by affinity chromatography, which specifically bind to the antigenic proteins CWP1, alpha-giardin 7.3 and kinesin 3.

(Continued)

A.

B.

In an additional aspect, the invention relates to a method for diagnosing giardiasis by detection of *Giardia* in a specific sample, and a kit for diagnosing giardiasis in biological and environmental samples.

6 Claims, 20 Drawing Sheets

Specification includes a Sequence Listing.

(56) References Cited

OTHER PUBLICATIONS

Moreno-Gonzalez et al., teach Production and purification of avian antibodies (IgYs) from Giardia intestinalis recombinant protein. Rev.Colomb.Quim. [online]. 2013, vol. 42, n.2, pp. 12-20. ISSN 0120-2804. (Year: 2013).*
Duque-Beltrán et al., (Mem. Inst. Oswaldo Cruz 97 (8) • Dec. 2002; 97(8): 1165-8). (Year: 2002).*
Berkman, D. S., et al. Effects of stunting, diarrhoeal disease, and parasitic infection during infancy on cognition in late childhood: a follow-up study. Lancet (2002). 359(9306), 564-571, (London, England).
Bertrand, I., et al. Improved specificity for Giardia lamblia cyst quantification in wastewater by development of a real-time PCR method. Journal of microbiological methods, (2004). 57(1), 41-53.
Serrano D.P., et al. Detección de antigenos de Giardia duodenalis en eludido de heces mediante ELISA indirecto utilizando anticuerpos policlonales. II Congreso Nacional de Investigación—Institute Nacional de Salud—Revista del Instituto Nacional de Colombia, (2002). 22(1), 154-155.
Stibbs, H. H., et al. Enzyme immunoassay for detection of Giardia lamblia cyst antigens in formalin-fixed and unfixed human stool. Journal of clinical microbiology, (1988). 26(9), 1665-1669.
Torabi, Z., et al.. Consistency of direct microscopic examination and ELISA in detection of Giardia in stool specimen among children. Asian Pacific Journal of Tropical Disease. (2014). 4(2), 725-727.
Torres, D., et al. Ensayo inmunoenzimático en fase sólida para la detección de antigenos de Giardia lamblia. Revista Cubana de Medicina Tropical. (1997). 49. 52-58.
Gómez J.E, et al. Giadiasis en niños viviendo en asentamientos temporales de Armenia. III Encuentro nacional de Investigación en Enfermedades infecciosas. Infectio—Revista de la asociación colombiana de infectología. (2002). 6(2), 89.
Towbin, H., et al. Electrophoretic transfer of proteins from polyacrylamide gels to nitrocellulose sheets: procedure and some applications. Proceedings of the National Academy of Sciences of the United States of America, (1979). 76(9), 4350-4354.
Ungar. L.,B., et al. Enzyme-linked immunosorbent assay for the detection of Giardia lamblia in fecal specimens. The Journal of infectious diseases, (1984). 149(1), 90-97.
Van Den Bossche, D., et al. Comparison of four rapid diagnostic tests, ELISA, microscopy and PCR for the detection of Giardia lamblia, *Cryptosporidium* spp. and Entamoeba histolytica in feces. Journal of microbiological methods, (2015). 110, 78-84.
Lopez-Romero, G., et al. (2015), Host defences against Giardia lamblia. Parasite Immunol, 37: 394-406. doi:10.1111/pim.12210.
Moreno-González, P. A. (2013) Estudio de la nicotinamida/nicotinato mononucleótido adenililtransferasa de Giardia lamblia (gNMNAT): determinatión de la localización subcelular y aproximación estructural. Master's Thesis, National University of Colombia. URL: http://bdigital.unal.edu.co/57937/1/01188158%202013.pdf.
Jahan N., Khatoon R. Y Ahmad S., (2014). A comparison of microscopy and enzyme linked immunosorbent assay for diagnosis of Giardia lamblia in Human faecal specimens. Journal of Clinical and Diagnostic Research, 8(11). DOI: 10.7860/JCDR/2014/9484. 5087. URL: https://www.ncbi.nlm.nih.gov/pmc/articles/PMC4290233/pdf/jcdr-8-015-DC04.pdf.

Boggild, A. K. et al.. Post-translational glutamylation and tyrosination in tubulin of tritrichomonads and the diplomonad Giardia intestinalis. Parasitology research, (2002). 88(1), 58-62.
Bossuyt, P. M., et al.. Towards complete and accurate reporting of studies of diagnostic accuracy: The STARD Initiative. Radiology, (2003). 226(1), 24-28.
Cacció, S. M., et al.. . Giardia cysts in wastewater treatment plants in Italy. Applied and environmental microbiology, (2003) 69(6), 3393-3398.
Carranza, P. G., et al. Simultaneous expression of different variant-specific surface proteins in single Giardia lamblia trophozoites during encystation. Infection and immunity, (2002). 70(9), 5265-5268.
Chan, R., et al. Evaluation of a combination rapid immunoassay for detection of Giardia and Cryptosporidium antigens. Journal of clinical microbiology, (2000). 38(1), 393-394.
Craft, J. C., & Nelson, J. D. Diagnosis of giardiasis by counterimmunoelectrophoresis of feces. The Journal of Infectious diseases, (1982). 145(4), 499-504.
Deshpande, S.P. Ethical climate and the link between success and ethical behavior: An empirical investigation of a non-profit organization. Journal of Business Ethics (1996) 15, 315-320.
Dias Da Silva, W., & Tambourgi, D. V. IgY: a promising antibody for use in immunodiagnostic and in immunotherapy. Veterinary immunology and immunopathology, (1996) 135(3-4), 173-180.
Duque-Beltrán, S., et al.. Detection of Giardia duodenalis antigen in human fecal eluates by enzyme-linked immunosorbent assay using polyclonal antibodies. Memorias do Instituto Oswaldo Cruz, (2002). 97(8), 1165-1168.
"Faubert G.M. & Belosevic M. Clinical symptoms and diagnosis by traditional methods. In EA Meyer, Giardiasis, vol. 3. HumanParasitic Diseases, Animal models for Giardia diodenalis type organisms. Elsevier Science Publishers Biomedical. Division, Amsterdam,(1990). 3, 77-90."
García, D.A.; et al. Obtención, purificación y caracterización de anticuerpos policlonales IgY desarrollados en gallina, dirigidos contra aislamientos colombianos de Giardia duodenalis. Biomed. (2005). 25: 451-463. (Bogotá).
Garcia, L. S., & Shimizu, R. Y. Evaluation of nine immunoassay kits (enzyme immunoassay and direct fluorescence) for detection of Giardia lamblia and Cryptosporidium parvum in human fecal specimens. Journal of clinical microbiology, (1997). 35(6), 1526-1529.
Geurden, T., et al. Prevalence and molecular characterisation of Cryptosporidium and Giardia in lambs and goat kids in Belgium. Veterinary parasitology, (2008). 155(1-2), 142-145.
Goka, A. K., et al. The relative merits of faecal and duodenal juice microscopy in the diagnosis of giardiasis. Transactions of the Royal Society of Tropical Medicine and Hygiene (1990). 84(1), 66-67.
Gómez, J.E., et al. Desarrollo y registro de un estuche inmunodiagnóstico para la detección de antígeno de cepas colombianas de Giardia duodenalis en eluidos de heces humanas mediante dot-Elisa. II Congreso Nacional de Investigación y salud—Instituto Nacional de Salud, (2002). 22(1), 79-80.
Gómez-Couso, H., et al. Giardia in shellfish-farming areas: detection in mussels, river water and waste waters. Veterinary parasitology, (2005). 133(1), 13-18.
Gonzales A., & Checchini S. Diagnóstico e investigación epidemiológica de las enfermedades transmitidas por os alimentos. Modulo 3. Enfermedades parasitarias trasmitidas por alimentos. Organización Panamericana de la Salud. URL: https://www.paho.org/arg/publicaciones/publicaciones%20virtuales/libroETAs/modulo3/modulo3c.html.
Hassan, S. M. T., et al.. Binding Properties and Immunolocalization of a Fatty Acid-Binding Protein in Giardia lamblia. Journal of Parasitology (2005) 91(2), 284-292.
Hernández, J.F.,et al. Identificación de antígenos de aislamientos colombianos deGiardia duodenalis reconocidos por IgG total y subclases. Biomedica, (2003). 23(3),263-273.
Keister D. B. Axenic culture of Giardia lamblia in TYI-S-33 medium supplemented with bile. Transactions of the Royal Society of Tropical Medicine and Hygiene, (1983). 77(4), 487-488.
Kim, J., et al. Interaction of beta-giardin with the Bop1 protein in Giardia lamblia. Parasitology research, (2006). 98(2), 138 144.

(56) References Cited

OTHER PUBLICATIONS

Knisley, C. V., et al. Rapid detection of giardia antigen in stool with the use of enzyme immunoassays. American journal of clinical pathology, (1989). 91(6), 704-708.
Koehler, A.V., et al. Giardia/giardiasis—A perspective on diagnostic and analytical tools. Biotechnology Advances. (2014). 32. 280-289.
Laemmli U. K. Cleavage of structural proteins during the assembly of the head of bacteriophage T4. Nature, (1970). 227(5259), 680-685.
Lemos, V., et al. Identification and determination of the viability of Giardia lamblia cysts and Cryptosporidium parvum and Cryptosporidium hominis oocysts in human fecal and water supply samples by fluorescent in situ hybridization (FISH) and monoclonal antibodies. Parasitology research. (2006). 98. 48-53.
Lipman, N. S., et al. Monoclonal Versus Polyclonal Antibodies: Distinguishing Characteristics, Applications, and Infomation Resources, ILAR Journal, (2005). 46(3), 258-268.
Lloyd, D., et al.. Giardia intestinalis, a eukaryote without hydrogenosomes, produces hydrogen. Microbiology (Reading, England), (2002). 148(Pt3), 727-733.
Mighell, A. J., et al.. An overview of the complexities and subtleties of immunohistochemistry. Oral diseases, (1998). 4(3), 217-223.
Muhsen K., & Levine M.M. A systematic review and meta-analysis of the association between Giardia lamblia and endemic pediatric diarrhea in developing countries. Clinical infectious diseases : an official publication of the Infectious Diseases Society of America, (2012). 55(4), 271-293.
Nash, T. E., et al. Usefulness of an enzyme-linked immunosorbent assay for detection of Giardia antigen in feces. Journal of clinical microbiology, (1987). 25(7), 1169-1171.
Olmos, R., et al. Identificación de antigenos de quistes y trofozoítos de aislamientos colombianos de Giardia duodenalis reconocidos por IgA. Biomédica. (2003). 23. 309-317.
Peralta, M.L., et al., Detectiom of 31, 65 and 170 kDa Giardia lamblia antigens in human fecal eluates specimens by Elisa. XVth International congress for tropical medicine and malaria. (2000). (FrPS2-12). 233.
Rader, C., et al. The rabbit antibody repertoire as a novel source for the generation of therapeutic human antibodies. The Journal of biological chemistry, (2000). 275(18), 13668-13676.
Ridley, D. S., & Hawgood, B. C. The value of formol-ether concentration of faecal cysts and ova. Journal of clinical pathology, (1956). 9(1), 74 76.
Rosenblatt, J. E., et al.. Evaluation of an enzyme-linked immunosorbent assay for the detection of Giardia lamblia in stool specimens. Diagnostic microbiology and infectious disease, (1993). 16(4), 337-341.
Rosoff, J. D., et al. Stool diagnosis of giardiasis using a commercially available enzyme immunoassay to detect Giardia-specific antigen 65 (GSA 65). Journal of clinical microbiology, (1989). 27(9), 1997-2002.
Schade, R., et al. The production of avian (egg yolk) antibodies: IgY. The report and recommendations of ECVAM worskshop 21. ATLA (1996). (vol. 24).
Vinayak, V. K., et al. An immunoenzymatic dot-ELISA for the detection of Giardia lamblia antigen in stool eluates of clinical cases of giardiasis. Journal of immunological methods, (1991). 137(2), 245-251.
Zhang, Y., et al. Risk assessment of Giardia from a full scale MBR sewage treatment plant caused by membrane integrity failure. Journal of environmental sciences (China), (2015). 30, 252-258.
Abdul-Wahid, A., & Faubert, G.M. Similarity in cyst wall protein (CWP) trafficking between encysting Giardia duodenalis trophozoites and CWP-expressing human embryonic kidney-293 cells. Biochemical and biophysical research communications, (2004). 324 3, 1069-80.
Addiss, D. G., et al. Evaluation of a commercially available enzyme-linked immunosorbent assay for Giardia lamblia antigen in stool. Journal of clinical microbiology, (1991). 29(6), 1137-1142.
Aldeen, W. E., et al. Evaluation of a commercially available ELISA assay for detection of Giardia lamblia in fecal specimens. Diagnostic Microbiology and Infectious Disease, (1995). 21(2), 77-79.
Aldeen, W. E., et al. Comparison of nine commercially available enzyme-linked immunosorbent assays for detection of Giardia lamblia in fecal specimens. Journal of clinical microbiology, (1998). 36(5), 1338-1340.
Arbo, A., et al. Opsonic requirements for the respiratory burst of neutrophils against Giardia lamblia trophozoites. Archives of medical research, (2006). 37(4), 465-473.
Arévalo, A., et al. Comportamiento de la infección experimental por aislamientos colombianos de Giardia duodenalis en el modelo animal del gerbo (Meriones unguiculatus). Biomédica—Revista del instituto Nacional de Colombia, (2005). 25(3), 305-14.
Arévalo, A., et al., Detección de antígenos de Giardia en materia fecal de *Meriones unguiculatus* (Gerbil) por ELISA utilizando anticuerpos policlonales. VI Encuentro cientlfico—Bioméica—Revista del instituto Nacional de Colombia, (1999). 19(1), 154-155.
Bazán-Tejeda, M. L., et al. Protein kinase C isoforms from Giardia duodenalis: identification and functional characterization of a beta-like molecule during encystment. Archives of microbiology, (2007). 187(1), 55-66.

\* cited by examiner

A.

B.

A.

| | | | |
|---|---|---|---|
| 1. | PM Kb | 7. | Colony 6 |
| 2. | Colony 1 | 8. | Colony 7 |
| 3. | Colony 2 | 9. | Colony 8 |
| 4. | Colony 3 | 10. | Colony 9 |
| 5. | Colony 4 | 11. | Colony 10 |
| 6. | Colony 5 | 12. | Negative control |

B.

A.

1. PM
2. Non-induced Protein
3. Induced Protein
4. Native lysis 1
5. Native lysis 2
6. Native lysis 3
7. Native lysis 4
8. Denaturing lysis
9. PM

B.

1. PM
2. Induced Protein
3. Non-induced Protein
4. Native lysis 1
5. Native lysis 2
6. Native lysis 3
7. Native lysis 4
8. Native lysis 5
9. Denaturing lysis

| Band No. | Band Label | Mol. Wt. (KDa) | Relative Front | Volumen (Int) |
|---|---|---|---|---|
| 1 | | N/A | 0,373 | 3.601.136 |

| Abs. Quant. (mg) | Rel. Quant. | Band % | Lane % |
|---|---|---|---|
| 91,8 | 1,04 | 100,0 | 45,6 |

1. PM
2. Colony 1
3. Colony 2
4. Colony 3
5. Colony 4
6. Colony 6
7. Colony 7
8. Control 1. PM
2. Non-digested plasmide Colony 1
3. Digested plasmide Colony 1
4. Non-digested plasmide Colony 2
5. Digested plasmide Colony 2
6. Non-digested plasmide Colony 3
7. Digested plasmide Colony 3
8. Non-digested plasmide Colony 4
9. Digested plasmide Colony 4
10. PM

SEQUENCE LISTING

```
<160> NUMBER OF SEQ ID NOS: 5

<210> SEQ ID NO 1
<211> LENGTH: 253
<212> TYPE: PRT
<213> ORGANISM: Giardia

<400> SEQUENCE: 1

Met Arg Gly Ser His His His His His His Gly Ser Met Met Leu Ala
1               5                   10                  15

Phe Leu Ala Leu Ala Gly Ser Ala Leu Ala Leu Thr Cys Pro Ala Thr
            20                  25                  30

Gln Arg Glu Val Leu Val Glu Ile Tyr Asp Ala Thr Asp Gly Ala Asn
```

```
                35                  40                  45
Trp Lys Thr Asn Asn Trp Leu Ser Gly Asp Ser Ile Cys Thr Trp Thr
 50                  55                  60
Gly Val Thr Cys Glu Ala Ser Asn Asn Tyr Val Ile Ala Leu Asp Leu
 65                  70                  75                  80
Ser Asp Met Gly Leu Thr Gly Thr Ile Pro Glu Asn Ile Gly Cys Leu
                 85                  90                  95
Thr Tyr Leu Lys Thr Leu Tyr Leu Ser Asn Asn Ser Leu Ala Gly Ala
                100                 105                 110
Ile Pro Glu Gly Leu Cys Gln Leu Thr Asn Leu Gln Tyr Leu Gln Val
                115                 120                 125
Asn Ser Ala Gly Leu Thr Gly Asp Ile Pro Glu Cys Met Cys Asp Leu
130                 135                 140
Ile His Leu Met Phe Trp Tyr Met Ser Asp Asn Ala Leu Thr Gly Ser
145                 150                 155                 160
Ile Pro Thr Cys Ile Asn Glu Leu Gln Phe Leu Lys Glu Leu His Leu
                165                 170                 175
Asp Cys Asn Gln Leu Ser Gly Thr Val Pro Val Gly Leu Met Thr Leu
                180                 185                 190
Pro Tyr Leu Met Glu Leu Tyr Leu Asn Cys Asn Pro Asp Leu Thr Cys
                195                 200                 205
Pro Asp Ala Thr Gly Val Gln Phe Val Phe Lys Cys Gly Asp Val Asp
                210                 215                 220
Cys Glu Asn Cys Gly Thr Leu Pro Pro Thr Asn Cys Ala Gln Cys Phe
225                 230                 235                 240
Thr Asp Pro Asp Cys Gly Glu Tyr Cys Leu Thr Gln Pro
                245                 250
```

<210> SEQ ID NO 2
<211> LENGTH: 307
<212> TYPE: PRT
<213> ORGANISM: Giardia

<400> SEQUENCE: 2

```
Met Arg Gly Ser His His His His His Gly Ser Met Ala Ala Ala
  1               5                  10                  15
Lys Ala Thr Glu Ile Lys Ala Leu Ile Asp Ala Lys Asp Met Asp Gly
                 20                  25                  30
Leu Ala Arg Ser Val Ala Asp Phe Asp Asp Arg Gln Arg Ala Glu Ile
                 35                  40                  45
Tyr Ala Ala Phe Arg Ala Ala Asn Gly Lys Thr Ala Ser Glu Tyr Leu
 50                  55                  60
Asp Ala Leu Phe Lys Asn Gly Asp Tyr Lys Asp Leu Met Met Ile Val
 65                  70                  75                  80
Leu Asp Asp Glu Ile Asp Val Arg Cys Lys Leu Ile Lys Lys Ala Phe
                 85                  90                  95
Lys Gly Gly Asn Asp Glu Arg Cys Leu Thr Asp Ala Leu Leu Thr Thr
                100                 105                 110
Thr Pro Glu Val Tyr Ala Arg Val Lys Asp Arg Tyr His Gln Leu Phe
                115                 120                 125
Gly Asp Asp Phe Glu Ser Thr Leu Arg Lys Glu Ile Gly Ser Lys Thr
                130                 135                 140
Val Trp Ala Arg Met Val Asn Ser Trp Leu Ala Phe Cys Arg Ser Ala
145                 150                 155                 160
```

```
Arg Asn Asn Ala Gln Gly Asp Ala Glu Ala Leu Lys Ala Ala Leu Ile
            165                 170                 175

Gly Val Lys His Pro Asp Thr Asp Thr Val Ile Arg Leu Leu Gly Thr
        180                 185                 190

Thr Val Pro Ser Glu Trp Lys Gln Ile Ser Glu Ala Phe Glu Ser Ile
        195                 200                 205

Ala Lys Lys Thr Ile Glu Gln Ala Leu Ile Glu Ala Tyr Lys Gly Asp
    210                 215                 220

Asp Glu Leu Ala Leu Cys Cys Cys Asn Ala Thr Leu His Cys Pro Ala
225                 230                 235                 240

Arg Gly Ala Ala Tyr Leu Leu Ser Leu Ala Cys Gln Lys Lys Gly Asp
                245                 250                 255

Thr Asp Arg Cys Cys Arg Ile Thr Gly Met Leu Tyr Asp Gln Ala Glu
            260                 265                 270

Gln Cys Lys Val Leu Tyr Ala His Tyr Gly Asn Leu Ala Lys Asp Ile
        275                 280                 285

Arg Ala Thr Met Ser Lys Asn Leu Ala Glu Ala Cys Cys Val Leu Trp
    290                 295                 300

His Val Met
305

<210> SEQ ID NO 3
<211> LENGTH: 1107
<212> TYPE: PRT
<213> ORGANISM: Giardia

<400> SEQUENCE: 3

Met Arg Gly Ser His His His His His His Gly Ser Met Pro Val Thr
1               5                   10                  15

Gly Val Lys Val Ala Val Arg Val Arg Pro Phe Asn Ala Arg Glu Lys
            20                  25                  30

Arg Glu Ala Ala Arg Leu Cys Val Asp Met Pro Gly Gly Gly Lys Val
        35                  40                  45

Val Leu Arg Asp Ala Asp Ala Lys Lys Pro Asp Ala Ala Phe Val Tyr
    50                  55                  60

Asp His Ala Tyr Trp Ser His Asp Ala Ser Arg Pro Cys Ala Thr Gln
65                  70                  75                  80

Asp Thr Val Tyr Ala Asp Ile Gly Pro Ser Val Leu Asp Asn Ala Phe
                85                  90                  95

Glu Gly Tyr Asn Tyr Thr Leu Phe Ala Tyr Gly Gln Thr Gly Ser Gly
            100                 105                 110

Lys Ser Tyr Ser Met Met Gly Ala Pro Ala Ser Glu Ala Asp Ala Gly
        115                 120                 125

Ile Ile Pro Arg Val Gly Arg Glu Leu Phe Arg Arg Ala Ala Ala Ser
    130                 135                 140

Pro Ala Glu Thr Gln Val Ser Val Ser Phe Leu Glu Ile Tyr Asn Glu
145                 150                 155                 160

Arg Leu Arg Asp Leu Leu Val Pro Ala Ala Gly Ala Gln Glu Leu Arg
                165                 170                 175

Ile Arg Gln Asp Pro Ala Ala Gly Val Phe Val Gln Asn Leu Ser His
            180                 185                 190

His Ala Val Ala Asp Tyr Asp Ala Ile Gln Arg Leu Ile Glu Leu Gly
        195                 200                 205

Asp Arg Asn Arg Thr Val Ala Ala Thr Asn Met Asn Ala Thr Ser Ser
    210                 215                 220
```

```
Arg Ser His Ser Val Phe Ala Ile Glu Val Val Gln Thr Ala Val Leu
225                 230                 235                 240

Arg Asn Asp Ala Gly Glu Val Gly Arg His Val Lys Arg Ala Arg
            245                 250                 255

Val Ser Leu Val Asp Leu Ala Gly Ser Glu Arg Gln Gly Lys Thr Gly
                260                 265                 270

Ala Thr Gly Asp Arg Leu Thr Glu Gly Ile Ser Ile Asn Lys Ser Leu
            275                 280                 285

Thr Thr Leu Gly Arg Val Ile Glu Ala Leu Ala Tyr Asn Thr Thr Ala
290                 295                 300

Glu Gly Arg Arg Lys Pro Gln His Val Pro Tyr Arg Asp Ser Gln Leu
305                 310                 315                 320

Thr Tyr Leu Leu Gln Pro Ala Leu Gly Gly Asn Ser Met Thr Cys Met
                325                 330                 335

Ile Ala Ala Ile Ser Pro Ala Ser Thr Asn Tyr Asp Glu Ser Leu Ser
                340                 345                 350

Thr Leu Arg Tyr Ala Asp Arg Ala His Gln Ile Glu Asn Thr Val Thr
            355                 360                 365

Lys Asn Glu Ser Ala Gln Glu Lys Tyr Ile Arg Glu Leu Glu Asp Arg
370                 375                 380

Val Lys Glu Leu Glu Ala Leu Leu Ala Gly Gly Ala Pro Ala Gly Asp
385                 390                 395                 400

Ala Gly Ala Val Glu Pro Gly Leu Ser Asp Ala Glu Arg Leu Glu Leu
                405                 410                 415

Glu Ala Lys Ile Ala Glu Tyr Asp Arg Leu Leu Lys Glu Gly Asn Gln
            420                 425                 430

Ser Leu Glu Glu Lys Leu Ala Arg Ala Glu Gln Asn Arg Gln Glu Leu
            435                 440                 445

Gln Asp Lys Leu Lys Lys Met Gly Leu Ala Ala Phe Gly Ser Glu
450                 455                 460

Ile Thr Thr Pro Tyr Ile Ser Asn Leu Ser Ser Asn Ala Ser Asp Asn
465                 470                 475                 480

Gly Gln Leu Ile Tyr Thr Leu Cys Ser Glu Asn Asp Leu Lys Asp Ala
                485                 490                 495

Arg Pro Val Thr Val Val Gly Ala Asp Asp Ser Gly Pro Thr Glu
            500                 505                 510

Cys Gln Cys Arg Ile Ala Leu Val Ser Lys Leu Gly Val Leu Gly Glu
            515                 520                 525

His Phe Ile Ile Ser Leu Thr Gly Lys Val Val Asp Ser Thr Ala Asn
            530                 535                 540

Pro Ile Phe Pro Lys Val Thr Glu Ala Thr Ile Arg Pro Leu Ser Ala
545                 550                 555                 560

Lys Gly Ala Leu Tyr Ile Asn Gly Arg Gln Ile Ala Ala Gly Ser Thr
                565                 570                 575

His Gln Leu Arg His Gly Asp Arg Ile Lys Cys Gly Ser Ala Ala Gln
            580                 585                 590

Ser Ser Phe Tyr Arg Tyr Tyr Asp Pro Pro Ala Arg Ala Ala Ala Val
            595                 600                 605

Lys Gln Ser Leu Glu Gln Asp Tyr Asp Tyr Val Glu Pro Glu Ile Thr
            610                 615                 620

Tyr Asp Leu Ala Leu Arg Glu Tyr Thr Tyr Tyr Gln Ser Ser Gly Lys
625                 630                 635                 640
```

-continued

```
Asp Thr Ala Gln Arg Pro Ile Gly Asp Asp Pro Val Ser Lys Glu Asn
            645                 650                 655

Val Ser Val Thr Met Asp Asp Ala Phe Gly Ile Thr Pro Gly Leu Asp
            660                 665                 670

Asn Val Gln Thr Asp Ile Asn Glu Ser Phe Tyr Ala Asp Phe Gly Asn
            675                 680                 685

Asp Asp Glu Arg Thr Thr Tyr Glu Lys Lys Val His Glu Val Leu Arg
            690                 695                 700

Gln Leu Tyr Pro Phe Ile Cys Glu Ala Asn Ser Ile Ala Glu Tyr Phe
705                 710                 715                 720

Cys Tyr Asp Ile Arg Phe Ala Ala Gln Ala Arg Thr Ser Ile Ser Pro
            725                 730                 735

Thr Ser Leu Arg Gln Ala Ala Arg Cys Gln Thr Ile Arg Asn Met Ser
            740                 745                 750

Lys Asn His Pro Met Thr Lys Asp Leu Arg Ala Asp Gln Ile Asp Asp
            755                 760                 765

Asp Leu Ser Gly Ile Leu Val Glu Ile Leu Val Thr Ala Thr Ala Ala
            770                 775                 780

Pro Ser Lys Thr Arg Asp Arg Lys Leu Ile Arg Gln Val Trp Ala Leu
785                 790                 795                 800

Glu Lys Phe Gly Leu Arg Leu Ser Gly Met Arg Arg Met Tyr Gly Leu
            805                 810                 815

Ala Met Thr Leu Gly Lys Glu Ala Val Arg Arg Ala His Glu Ser
            820                 825                 830

Ala Asp Arg Asp Leu Glu Asp Asp Glu Phe Pro Phe Asp Leu Glu
            835                 840                 845

Ala Asp Ile Tyr Asn Gln Thr Leu Thr His Leu Ile Gly Val Gly Arg
850                 855                 860

Ile Pro Leu Ser Gly Leu Leu Glu Thr Cys Glu Thr Asp Val Phe Ser
865                 870                 875                 880

Val Pro Ile Tyr Asp Tyr Ser Gly Lys Ala Ala Thr Ser Ile Asp Val
            885                 890                 895

Ser Leu Ser Leu Leu Gly Ser Gly Tyr Ser His His Gly Ala Glu Cys
            900                 905                 910

Leu Ala Cys Asp Val Ala Asn Leu Val Gln Asn Glu Ser Pro Val Thr
            915                 920                 925

Thr Ile Ala Ala Tyr Phe Lys Lys Ala Tyr Asn Val Pro Thr Gln Cys
            930                 935                 940

Cys Lys Lys Val His Ala Val Ile His Met Pro Trp Phe Val Asn Pro
945                 950                 955                 960

Asp Ala Gly Arg Pro Lys Gly Lys Arg Leu Ser Val Tyr Gln Glu Asn
            965                 970                 975

Glu Phe Arg Arg Arg Leu Leu Asp Met Gly Tyr Thr Phe Gln Thr Ala
            980                 985                 990

Ser Ser Ser Asp Leu Ser Pro Asn Pro Ala Leu Asp Ser Thr Ile Tyr
            995                 1000                1005

Met Asp Leu Lys Thr Ser Tyr Phe Lys Gln Asp Asp Val Leu Glu
        1010                1015                1020

Trp Leu Arg Thr Ser Gly Thr Gly Leu Glu Val Ser Leu Tyr Gly
        1025                1030                1035

Tyr Thr Ser Ala Tyr Ala Asp Ser Leu Val Pro Glu Ile Lys Asp
        1040                1045                1050

Ser Ala Leu Pro Asp Pro Ser Lys Lys Lys Val Ala Ile Val Ser
```

```
              1055                1060                1065
Thr Asn Ile Val Arg Thr Gln Thr Lys Glu Asp Gly Phe Lys Glu
            1070                1075                1080

Ile Asn Gly Glu Gln Val Leu Ile Ile Lys Lys Phe Ile Phe Val
            1085                1090                1095

Asp Gln Thr Lys Thr Asp Thr Gly His
            1100                1105

<210> SEQ ID NO 4
<211> LENGTH: 4150
<212> TYPE: DNA
<213> ORGANISM: Giardia

<400> SEQUENCE: 4
```

| | | | | | |
|---|---|---|---|---|---|
| ctcgagaaat | cataaaaaat | ttatttgctt | tgtgagcgga | taacaattat | aatagattca | 60 |
| attgtgagcg | ataacaatt | tcacacagaa | ttcattaaag | aggagaaatt | aactatgaga | 120 |
| ggatcgcatc | accatcacca | tcacggatcc | atgatgctcg | cttttcttgc | tcttgcaggt | 180 |
| tctgcccttg | ccctcacttg | cccggctact | cagagggagg | tgctcgtcga | aatctacgat | 240 |
| gccactgacg | gagcaaattg | gaagaccaat | aattggcttt | cgggagactc | tatttgcacc | 300 |
| tggacaggtg | ttacgtgtga | ggcctcgaat | aactacgtta | tcgccctgga | tctttcggac | 360 |
| atgggcctta | caggtaccat | cccggagaac | atcggctgcc | ttacttacct | caagacccct | 420 |
| tacttgagca | caaactcatt | ggctggtgcc | atcccagagg | gtctgtgcca | attgacgaac | 480 |
| ctccagtact | gcaggtcaa | tagtgccggt | ctgacaggcg | atattcccga | gtgcatgtgc | 540 |
| gacctcattc | acctaatgtt | ctggtacatg | agtgacaacg | ctctcacagg | ctccatcccc | 600 |
| acctgcatca | atgagcttca | atttctcaag | gagctccacc | tagactgcaa | tcagctgtca | 660 |
| ggcacggtcc | ctgttggcct | tatgacgctc | ccctacctta | tggagctcta | tctcaactgc | 720 |
| aaccctgacc | tcacatgccc | cgatgcgact | ggagtgcagt | tcgtcttcaa | gtgcggagat | 780 |
| gtcgactgtg | agaactgcgg | aaccttgcca | ccaaccaact | gtgcccagtg | ctttactgat | 840 |
| ccggactgcg | gagagtactg | cctcactcaa | ccatgaagct | taattagctg | agcttggact | 900 |
| cctgttgata | gatccagtaa | tgacctcaga | actccatctg | gatttgttca | gaacgctcgg | 960 |
| ttgccgccgg | gcgtttttta | ttggtgagaa | tccaagctag | cttggcgaga | ttttcaggag | 1020 |
| ctaaggaagc | taaaatggag | aaaaaaatca | ctggatatac | caccgttgat | atatcccaat | 1080 |
| ggcatcgtaa | agaacatttt | gaggcatttc | agtcagttgc | tcaatgtacc | tataaccaga | 1140 |
| ccgttcagct | ggatattacg | gcctttttaa | agaccgtaaa | gaaaaataag | cacaagtttt | 1200 |
| atccggcctt | tattcacatt | cttgcccgcc | tgatgaatgc | tcatccggaa | tttcgtatgg | 1260 |
| caatgaaaga | cggtgagctg | gtgatatggg | atagtgttca | cccttgttac | accgttttcc | 1320 |
| atgagcaaac | tgaaacgttt | tcatcgctct | ggagtgaata | ccacgacgat | ttccggcagt | 1380 |
| ttctacacat | atattcgcaa | gatgtggcgt | gttacggtga | aaacctggcc | tatttcccta | 1440 |
| aagggtttat | tgagaatatg | ttttcgtct | cagccaatcc | ctgggtgagt | ttcaccagtt | 1500 |
| ttgatttaaa | cgtggccaat | atggacaact | tcttcgcccc | cgttttcacc | atgggcaaat | 1560 |
| attatacgca | aggcgacaag | gtgctgatgc | cgctggcgat | tcaggttcat | catgccgttt | 1620 |
| gtgatggctt | ccatgtcggc | agaatgctta | atgaattaca | acagtactgc | gatgagtggc | 1680 |
| agggcggggc | gtaattttt | taaggcagtt | attggtgccc | ttaaacgcct | ggggtaatga | 1740 |
| ctctctagct | tgaggcatca | aataaaacga | aaggctcagt | cgaaagactg | ggcctttcgt | 1800 |

-continued

```
tttatctgtt gtttgtcggt gaacgctctc ctgagtagga caaatccgcc ctctagagct    1860
gcctcgcgcg tttcggtgat gacggtgaaa acctctgaca catgcagctc ccggagacgg    1920
tcacagcttg tctgtaagcg gatgccggga gcagacaagc ccgtcagggc gcgtcagcgg    1980
gtgttggcgg gtgtcgggc gcagccatga cccagtcacg tagcgatagc ggagtgtata     2040
ctggcttaac tatgcggcat cagagcagat tgtactgaga gtgcaccata tgcggtgtga    2100
aataccgcac agatgcgtaa ggagaaaata ccgcatcagg cgctcttccg cttcctcgct    2160
cactgactcg ctgcgctcgg tcgttcggct gcggcgagcg gtatcagctc actcaaaggc    2220
ggtaatacgg ttatccacag aatcagggga taacgcagga agaacatgt gagcaaaagg     2280
ccagcaaaag gccaggaacc gtaaaaaggc cgcgttgctg gcgttttcc ataggctccg      2340
cccccctgac gagcatcaca aaatcgacg ctcaagtcag aggtggcgaa acccgacagg     2400
actataaaga taccaggcgt ttccccctgg aagctccctc gtgcgctctc ctgttccgac    2460
cctgccgctt accggatacc tgtccgcctt tctcccttcg ggaagcgtgg cgctttctca    2520
tagctcacgc tgtaggtatc tcagttcggt gtaggtcgtt cgctccaagc tgggctgtgt    2580
gcacgaaccc cccgttcagc ccgaccgctg cgccttatcc ggtaactatc gtcttgagtc    2640
caacccggta agacacgact tatcgccact ggcagcagcc actggtaaca ggattagcag    2700
agcgaggtat gtaggcggtg ctacagagtt cttgaagtgg tggcctaact acggctacac    2760
tagaaggaca gtatttggta tctgcgctct gctgaagcca gttaccttcg gaaaaagagt    2820
tggtagctct tgatccggca aacaaaccac cgctggtagc ggtggttttt tgtttgcaa     2880
gcagcagatt acgcgcagaa aaaaggatc tcaagaagat cctttgatct tttctacggg     2940
gtctgacgct cagtggaacg aaaactcacg ttaagggatt ttggtcatga gattatcaaa    3000
aaggatcttc acctagatcc ttttaaatta aaaatgaagt tttaaatcaa tctaaagtat    3060
atatgagtaa acttggtctg acagttacca atgcttaatc agtgaggcac ctatctcagc    3120
gatctgtcta tttcgttcat ccatagttgc ctgactcccc gtcgtgtaga taactacgat    3180
acgggagggc ttaccatctg gccccagtgc tgcaatgata ccgcgagacc cacgctcacc    3240
ggctccagat ttatcagcaa taaaccagcc agcggaagg gccgagcgca gaagtggtcc      3300
tgcaacttta tccgcctcca tccagtctat taattgttgc cgggaagcta gagtaagtag    3360
ttcgccagtt aatagtttgc gcaacgttgt tgccattgct acaggcatcg tggtgtcacg    3420
ctcgtcgttt ggtatggctt cattcagctc cggttcccaa cgatcaaggc gagttacatg    3480
atcccccatg ttgtgcaaaa aagcggttag ctccttcggt cctccgatcg ttgtcagaag    3540
taagttggcc gcagtgttat cactcatggt tatggcagca ctgcataatt ctcttactgt    3600
catgccatcc gtaagatgct tttctgtgac tggtgagtac tcaaccaagt cattctgaga    3660
atagtgtatg cggcgaccga gttgctcttg cccggcgtca atacgggata ataccgcgcc    3720
acatagcaga actttaaaag tgctcatcat tggaaaacgt tcttcggggc gaaaactctc    3780
aaggatctta ccgctgttga gatccagttc gatgtaaccc actcgtgcac ccaactgatc    3840
ttcagcatct tttactttca ccagcgtttc tgggtgagca aaaacaggaa ggcaaaatgc    3900
cgcaaaaaag ggaataaggg cgacacgaaa atgttaata ctcatactct ccttttttca     3960
atattattga agcatttatc agggttattg tctcatgagc ggatacatat ttgaatgtat    4020
ttagaaaaat aaacaaatag gggttccgcg cacatttccc cgaaaagtgc cacctgacgt    4080
ctaagaaacc attattatca tgacattaac ctataaaaat aggcgtatca cgaggccctt    4140
tcgtcttcac                                                          4150
```

<210> SEQ ID NO 5
<211> LENGTH: 4343
<212> TYPE: DNA
<213> ORGANISM: Giardia

<400> SEQUENCE: 5

| | | | | | |
|---|---|---|---|---|---|
| ctcgagaaat | cataaaaaat | ttatttgctt | tgtgagcgga | taacaattat | aatagattca | 60 |
| attgtgagcg | gataacaatt | tcacacagaa | ttcattaaag | aggagaaatt | aactatgaga | 120 |
| ggatcgcatc | accatcacca | tcacggatcc | atggctgcag | caaaggctac | cgagatcaag | 180 |
| gcgctcatcg | acgccaagga | catggacggg | cttgcgagga | gcgtcgccga | cttcgacgac | 240 |
| aggcagcgcg | ccgagatcta | cgccgcgttc | agggcggcca | acgggaagac | ggcctccgag | 300 |
| tacctcgacg | ccttgttcaa | gaacggggac | tacaaggacc | tcatgatgat | cgtcctcgac | 360 |
| gacgagatcg | acgtccgctg | caagctgatc | aagaaggcct | tcaagggcgg | gaacgacgag | 420 |
| aggtgcctca | cggacgcgct | cctgacgacg | accccccgagg | tctacgcaag | ggtcaaggac | 480 |
| aggtaccacc | agctcttcgg | ggacgacttc | gagtccacgc | tcaggaagga | gatcggctcc | 540 |
| aagaccgtct | gggcccgcat | ggtgaactcc | tggcttgcct | tctgcaggtc | tgcccgcaac | 600 |
| aacgcccagg | gtgatgcaga | ggccctgaag | gccgcgctga | tcggcgtcaa | gcacccggac | 660 |
| acggacacgg | tcatccgcct | cctcggcacg | accgtcccca | gcgagtggaa | gcagatctcc | 720 |
| gaggcgttcg | agagcatcgc | caagaagacg | atcgagcagg | ccctcatcga | ggcctacaag | 780 |
| ggcgacgacg | agctcgcgct | ctgctgctgc | aacgcgacgc | tccactgccc | cgcccgaggc | 840 |
| gccgcctacc | tcctgagcct | ggcttgccag | aagaagggcg | acaccgaccg | ctgctgccgc | 900 |
| atcaccggga | tgctctacga | tcaggcggag | cagtgcaagg | tcctctacgc | ccactacggc | 960 |
| aacttagcca | aggacatccg | agccacgatg | tccaagaacc | tcgccgaggc | ctgctgcgtc | 1020 |
| ctctggcacg | tcatgtaaga | gctcggtacc | ccgggtcgac | ctgcagccaa | gcttaattag | 1080 |
| ctgagcttgg | actcctgttg | atagatccag | taatgacctc | agaactccat | ctggatttgt | 1140 |
| tcagaacgct | cggttgccgc | cgggcgtttt | ttattggtga | gaatccaagc | tagcttggcg | 1200 |
| agattttcag | gagctaagga | agctaaaatg | gagaaaaaaa | tcactggata | taccaccgtt | 1260 |
| gatatatccc | aatggcatcg | taaagaacat | tttgaggcat | ttcagtcagt | tgctcaatgt | 1320 |
| acctataacc | agaccgttca | gctggatatt | acggcctttt | aaagaccgt | aaagaaaaat | 1380 |
| aagcacaagt | tttatccggc | ctttattcac | attcttgccc | gcctgatgaa | tgctcatccg | 1440 |
| gaatttcgta | tggcaatgaa | agacggtgag | ctggtgatat | gggatagtgt | tcacccttgt | 1500 |
| tacaccgttt | tccatgagca | aactgaaacg | ttttcatcgc | tctggagtga | ataccacgac | 1560 |
| gatttccggc | agtttctaca | catatattcg | caagatgtgg | cgtgttacgg | tgaaaacctg | 1620 |
| gcctatttcc | ctaaagggtt | tattgagaat | atgttttcg | tctcagccaa | tccctgggtg | 1680 |
| agtttcacca | gttttgattt | aaacgtggcc | aatatggaca | acttcttcgc | cccgttttc | 1740 |
| accatgggca | atattatac | gcaaggcgac | aaggtgctga | tgccgctggc | gattcaggtt | 1800 |
| catcatgccg | tttgtgatgg | cttccatgtc | ggcagaatgc | ttaatgaatt | acaacagtac | 1860 |
| tgcgatgagt | ggcagggcgg | ggcgtaattt | ttttaaggca | gttattggtg | cccttaaacg | 1920 |
| cctggggtaa | tgactctcta | gcttgaggca | tcaaataaaa | cgaaaggctc | agtcgaaaga | 1980 |
| ctgggccttt | cgttttatct | gttgtttgtc | ggtgaacgct | ctcctgagta | ggacaaatcc | 2040 |
| gccctctaga | gctgcctcgc | gcgtttcggt | gatgacggtg | aaaacctctg | acacatgcag | 2100 |

```
ctcccggaga cggtcacagc ttgtctgtaa gcggatgccg ggagcagaca agcccgtcag    2160
ggcgcgtcag cgggtgttgg cgggtgtcgg ggcgcagcca tgacccagtc acgtagcgat    2220
agcggagtgt atactggctt aactatgcgg catcagagca gattgtactg agagtgcacc    2280
atatgcggtg tgaaataccg cacagatgcg taaggagaaa ataccgcatc aggcgctctt    2340
ccgcttcctc gctcactgac tcgctgcgct cggtcgttcg gctgcggcga gcggtatcag    2400
ctcactcaaa ggcggtaata cggttatcca cagaatcagg ggataacgca ggaaagaaca    2460
tgtgagcaaa aggccagcaa aaggccagga accgtaaaaa ggccgcgttg ctggcgtttt    2520
tccataggct ccgcccccct gacgagcatc acaaaaatcg acgctcaagt cagaggtggc    2580
gaaacccgac aggactataa agataccagg cgtttccccc tggaagctcc ctcgtgcgct    2640
ctcctgttcc gaccctgccg cttaccggat acctgtccgc ctttctccct tcgggaagcg    2700
tggcgctttc tcatagctca cgctgtaggt atctcagttc ggtgtaggtc gttcgctcca    2760
agctgggctg tgtgcacgaa ccccccgttc agcccgaccg ctgcgcctta tccggtaact    2820
atcgtcttga gtccaacccg gtaagacacg acttatcgcc actggcagca gccactggta    2880
acaggattag cagagcgagg tatgtaggcg gtgctacaga gttcttgaag tggtggccta    2940
actacggcta cactagaagg acagtatttg gtatctgcgc tctgctgaag ccagttacct    3000
tcggaaaaag agttggtagc tcttgatccg gcaaacaaac caccgctggt agcggtggtt    3060
tttttgtttg caagcagcag attacgcgca gaaaaaagg atctcaagaa gatcctttga    3120
tcttttctac ggggtctgac gctcagtgga acgaaaactc acgttaaggg attttggtca    3180
tgagattatc aaaaaggatc ttcacctaga tccttttaaa ttaaaaatga agttttaaat    3240
caatctaaag tatatatgag taaacttggt ctgacagtta ccaatgctta atcagtgagg    3300
cacctatctc agcgatctgt ctatttcgtt catccatagt tgcctgactc cccgtcgtgt    3360
agataactac gatacgggag ggcttaccat ctggccccag tgctgcaatg ataccgcgag    3420
acccacgctc accggctcca gatttatcag caataaacca gccagccgga agggccgagc    3480
gcagaagtgg tcctgcaact ttatccgcct ccatccagtc tattaattgt tgccgggaag    3540
ctagagtaag tagttcgcca gttaatagtt tgcgcaacgt tgttgccatt gctacaggca    3600
tcgtggtgtc acgctcgtcg tttggtatgg cttcattcag ctccggttcc caacgatcaa    3660
ggcgagttac atgatccccc atgttgtgca aaaaagcggt tagctccttc ggtcctccga    3720
tcgttgtcag aagtaagttg gccgcagtgt tatcactcat ggttatggca gcactgcata    3780
attctcttac tgtcatgcca tccgtaagat gcttttctgt gactggtgag tactcaacca    3840
agtcattctg agaatagtgt atgcggcgac cgagttgctc ttgcccggcg tcaatacggg    3900
ataataccgc gccacatagc agaactttaa aagtgctcat cattggaaaa cgttcttcgg    3960
ggcgaaaact ctcaaggatc ttaccgctgt tgagatccag ttcgatgtaa cccactcgtg    4020
cacccaactg atcttcagca tcttttactt tcaccagcgt ttctgggtga gcaaaaacag    4080
gaaggcaaaa tgccgcaaaa aagggaataa gggcgacacg gaaatgttga atactcatac    4140
tcttcctttt tcaatattat tgaagcattt atcagggtta ttgtctcatg agcggataca    4200
tatttgaatg tatttagaaa aataaacaaa taggggttcc gcgcacattt ccccgaaaag    4260
tgccacctga cgtctaagaa accattatta tcatgacatt aacctataaa aataggcgta    4320
tcacgaggcc ctttcgtctt cac                                            4343
```

GIARDIA RECOMBINANT ANTIGENS, PURIFICATION OF POLYCLONAL ANTI-GIARDIA IGG AND IGY ANTIBODIES AND GIARDIA DETECTION

FIELD OF INVENTION

The present invention is framed in the field of biotechnology, particularly in products and methods for the specific detection of *Giardia* antigens in biological samples, in such a way that it is possible to detect the active infection even when the complete parasite or its stages (cysts and/or trophozoites) are not present in a given sample.

BACKGROUND OF THE INVENTION

Giardiasis Among the intestinal parasites with the greatest impact on public health worldwide is giardiasis, a disease caused by *Giardia*, a parasite (intestinal protozoa) that is transmitted in water (since it is resistant to the different chemical agents used in water purification (Yu Zhang et al., 2015), from contaminated food or through person-to-person by means of the fecal-oral route (Koehler et al., 2014).

*Giardia* lacks certain organelles (mitochondria and Golgi apparatus) and has two life forms in its life cycle, trophozoite and cyst. This protozoan is the main agent of acute diarrheal disease (ADD) in humans, particularly in children (Muhsen and Levine, 2012). The infection by this parasite manifests itself with a clinical spectrum that ranges from asymptomatic infection to symptomatic infection with chronic diarrhea, malabsorption syndrome and childhood delayed growth (Gonzalez and Cecchini, 2013), persisting for longer and with more intensity than infections by other intestinal parasites and causing adverse effects in both growth and development, as well as in learning (Berkman et al., 2002).

The prevalence of intestinal parasites is very high in marginalized or highly vulnerable populations, concentrating in early childhood, school children, pregnant women, rural and indigenous populations, and may vary according to the study group and the risk factors associated with giardiasis. In countries such as Colombia, the prevalence is 21.1% in children under 5 years of age (Castro and Nicholls, 1998), 65% in children under 13 years of age housed in temporary settlements (Torres et al., 2002) and 15.4% in Colombian school population (National Intestinal Parasitism Survey 2012-2014).

The identification of *Giardia* cysts or trophozoites is usually done in fecal samples (a serial or coprological sample) or with invasive methods such as duodenal aspirate, imprinting and small bowel biopsy (Goka et al., 1990, Wolfe, 1990) which are uncomfortable and expensive. However, given the intermittent excretion of the parasite in feces, false negatives may be generated.

The fundamental purpose in the diagnosis of parasitic diseases is identifying the parasite. In giardiasis, the identification of *Giardia* cysts or trophozoites depends on several factors such as: experience of the microscopist (Torabi et al., 2014, Van den Bossche, 2015); previous ingestion of substances that cause false negative results such as: non-medicated antiprotozoal remedies, antibiotics, antacids, anti-diarrheal, enemas, laxatives (Wolfe, 1978); the use of barium as a contrast medium in intestinal radiological examination (Sun, 1980) and the phenomenon of intermittent excretion of fecal *Giardia* cysts that is inherent in the biological nature of the parasite (Faubert and Belosevic, 1990; Torabi et al. 2014).

The host may be infected with *Giardia* but, due to the biological nature of the parasite, which cannot be modified, false negatives (reporting that no *Giardia* cysts are observed) may be incurred when the fecal sample is examined. For this reason, it is essential to resort to the detection of the parasite in feces by means of polyclonal anti-*Giardia* antibodies that allow the presence of the parasite to be determined even though it is not excreted in feces.

Anti-*Giardia* Polyclonal Antibodies

Anti-*Giardia* monoclonal antibodies have been developed in mice to understand aspects related to the parasite. Thus, between 1999 and 2006, studies were conducted on the simultaneous expression of different surface proteins of *Giardia* trophozoite during encystment (Carranza et al., 2002); glutamination and post-translational tyrosination in tubulin from *Giardia* intestinalis (Boggild et al., 2002); hydrogen production by *Giardia* (Lloyd et al., 2002); detection of *Giardia* by immunofluorescence (El-Shewy and El-Hamshary, 1999), identification of the parasite in water (Caccio et al., 2003, Bertrand et al., 2004, Gomez-Couso et al., 2005); viability of *Giardia* cysts in human fecal matter and water from the environment (Lemos et al., 2005), the similarity of the cystic wall protein of *Giardia* and the trophozoite of the encystating parasite (Abdul-Wahid and Faubert, 2004), the opsonization requirements related to the respiration of neutrophils against *Giardia* trophozoites (Arbo et al., 2006); detection of *Giardia* cyst in human fecal matter by means of the ELISA enzyme immunoassay or by immunodiagnostic kits, with sensitivities between 90% and 100% and specificities between 91% and 100%, using the monoclonal antibody as the first or second capturing agent (Chan, 2000) and in order to complete the capture of *Giardia* antigen, they have kept using polyclonal antibodies.

Polyclonal antibodies developed in rabbits have been used for diagnosis and in studies for the generation of human therapeutic antibodies (Rader et al., 2000). The use of birds, such as hens, in order to produce polyclonal antibodies, in comparison with that of mammals, is an important alternative because it reduces the number of animals to be immunized and eliminates invasive methods such as bleeding specimens (Dias and Tambourgi, 2010).

Anti-*Giardia* polyclonal antibodies continue to be developed to perform specific studies related to the parasite, such as the determination of the binding and immunolocalization properties of specific proteins of the parasite (Hassan et al., 2005), the interaction of beta giardin with nuclear protein Bopl (Kim et al., 2006), the protein kinase C isoforms of *Giardia duodenalis* (Bazan et al., 2007) and detection of *Giardia* in human fecal matter, as mentioned above.

Polyclonal antibodies have the advantage over monoclonal antibodies in that the former recognize multiple epitopes of the target antigen and bind to immunogenic epitopes, which, in some cases, can be disadvantageous because there is the chance of binding to similar epitopes of other proteins and cause false positives (Mighell et al., 1998). This disadvantage may be avoided using IgY polyclonal antibodies, such as those of the present invention.

IgY polyclonal antibodies have been developed against virus-specific antigens (rotavirus, enterovirus, picornavirus, arbovirus, paramyxovirus, potyvirus and adenovirus), bacteria (Enterotoxigenic and enteropathogenic *Escherichia coli, Brucella abortus*), parasites (*Sarcocystis igantea, Toxoplasma gondii* and *Echinococcus granulosas*), peptides and proteins (Schade et al., 1996). However, no IgY anti-*Giardia* polyclonal antibody developments have been identified for diagnosis against the entire stage of the parasite trophozoite.

Moreno-Gonzalez et al., 2013 obtained and purified avian antibodies (IgYs) from inclusion bodies of a recombinant protein from *Giardia* and which is key in the metabolism of NAD+, but with the purpose of studying the energy metabolism in basal organisms. Garcia et al, 2005 developed polyclonal IgY anti-trophozoite antibodies of *Giardia* in hens from Colombian isolates of the parasite. *Giardia* trophozoite contains the antigenic epitopes of the cyst and others related to its stage, inducing the pathology and the immune response in the host (Olmos et al., 2003, Hernandez et al., 2003).

Purification of Polyclonal Antibodies

The purification methods of antibodies may be divided into two major groups: fractionation and affinity purification. Ammonium sulfate precipitation, ion exchange chromatography (IEC), size exclusion chromatography (SEC), and metal chelate chromatography (IMAC) are among the fractionation methods.

Affinity purification methods may be:
  Class-specific purification: it consists of the solid phase binding of a certain class of antibodies (for example, IgG), by means of immobilized ligands having specific affinity with this class of immunoglobulins. It purifies all immunoglobulins of a certain class, regardless of their affinity for the antigen of interest.
  Antigen-specific purification: Separates immunoglobulins that bind specifically to an immobilized antigen. Purifies all antibodies that are specific for that antigen, independently from its class or isotype.

*Giardia* Detection

The detection of *Giardia duodenalis* in fecal matter, using polyclonal antibodies, has the following advantages: polyclonal antibodies can be developed more rapidly, at lower cost and with fewer technical and procedural requirements than those required for the development of monoclonal antibodies. The generation of monoclonal antibodies takes up to a year or longer, while polyclonal antibodies develop in months.

Polyclonal antibodies are heterogeneous and recognize different antigenic epitopes. Thus the effect given by any change or by a small number of epitopes is less critical. Polyclonal antibodies are more stable to changes in pH and salt concentrations than monoclonal antibodies that are highly susceptible to any change in the aforesaid factors (Lipman et al., 2005).

The *Giardia* antigen may be detected in feces by immunoassays: counter-immunoelectrophoresis (CIE) (Craft and Nelson, 1982), enzyme-linked immunosorbent assay (ELISA) (Ungar et al, 1984) and dot-ELISA (Vinayak et al, 1991). The sensitivity of the methods varies from 88% to 98% using ICD, from 68% to 100% by ELISA and 92% with dot-ELISA. The specificity of these tests vary between 90% and 97% for the ICD, between 81% and 100% for ELISA and for Dot-ELISA, it is 100%.

The advantage of the detection of excretion/secretion antigens of *Giardia* in feces, using IgY anti-*Giardia* polyclonal antibodies on the identification of the parasite by microscopy, is that they allow determining *Giardia* infection in the host even when the parasite cysts are not released in fecal matter (Nash et al., 1987). Additionally, following this methodology, a large number of samples may be processed (Geurden et al., 2008).

Standardizations and preliminary evaluations of the direct and indirect ELISA and dot-ELISA have been made for the detection of *Giardia* antigen in gerbil feces (Meriones unguiculatus), animal model for studies of giardiosis (Arévalo et al., 2005) and in human feces (Peralta et al, 2000; Gomez et al, 2002; Duque et al, 2002), with sensitivities ranging between 72% and 100% and specificities between 81% and 100%. The immunoassays mentioned for the detection of *Giardia* in feces have used polyclonal anti-*Giardia* IgG antibodies developed in rabbits (Tones et al., 1997, Arévalo, 1999, Peralta, et al., 2000, Serrano, 2001, Duque et al, 2002); goats (Ungar et al., 1984; Nash et al., 1987; Knisley et al., 1989) and using anti-*Giardia* monoclonal antibodies developed in mice (Chan, et al., 2000).

Immunoenzymatic assays based on direct or indirect ELISA have been commercialized in the form of diagnostic kits for the detection of *Giardia* antigen in fecal eluates. These have a sensitivity of 85%-100% and a specificity of 90%-100% (Sloan et al, 1989, Addiss et al, 1991). Aldeen et. al., in 1998, compared nine diagnostic kits for the detection of fecal *Giardia*, demonstrating the sensitivity of the test ranges between 96% and 100% and the specificity of the test between 99% and 100%. There are several commercially available immunodiagnostic kits to detect *Giardia* antigen in fecal matter whose sensitivity varies between 85% and 98% and its specificity between 90% and 100% (Addiss et al, 1991, Aldeen et al, 1995, Garcia and Shimizu, 1997). Rosenblatt et al, 1993; Rossoff et al, 1989; Stibbs et al, 1988). The sensitivity and specificity of the methods depends on the strain of *Giardia* circulating in a geographic area and the genetic variability inherent to the parasite (Torabi et al., 2014).

Despite the existence of several methods for the detection of *Giardia*, it is necessary to develop new alternative methods for obtaining and purifying anti-*Giardia* polyclonal antibodies, as well as in vitro diagnostic tests for the detection of *Giardia* antigens in different types of samples. Currently, very little is known of immunodiagnostic techniques that use *Giardia* polyclonal antibodies.

BRIEF DESCRIPTION OF THE INVENTION

The present invention relates to a reusable stationary phase for the purification of polyclonal anti-*Giardia* IgG and IgY antibodies, which comprises a mixture of at least two of the recombinant antigenic proteins CWP1, alpha giardin 7.3 and Kinesin 3 incorporated on a solid support.

The invention also contemplates a method for the purification of polyclonal anti-*Giardia* IgG and IgY antibodies by affinity chromatography with said stationary phase and the purified polyclonal anti-*Giardia* IgG and IgY antibodies that specifically bind to the antigenic proteins CWP1, alpha giardin 7.3 and Kinesin 3.

In another aspect, the invention relates to a method of diagnosing giardiasis, by detecting *Giardia* antigens in a biological sample, which uses said purified polyclonal anti-*Giardia* IgG and IgY antibodies. In a further aspect, the invention contemplates a kit for diagnosing giardiasis in biological samples comprising purified anti-*Giardia* IgG and IgY polyclonal antibodies, together with a conjugate of anti-*Giardia* antibody bound to a reporter and a detection reagent.

The detection of the parasite by the polyclonal anti-*Giardia* IgG and IgY antibodies of the present invention allows to diagnose infection even when the cysts of the parasite are not found in the sample, since, unlike conventional methods, they selectively identify the specific antigens of *Giardia* cysts and trophozoites: CWP1, alpha giardin 7.3 and Kinesin 3.

DETAILED DESCRIPTION OF THE INVENTION

Figure 1:
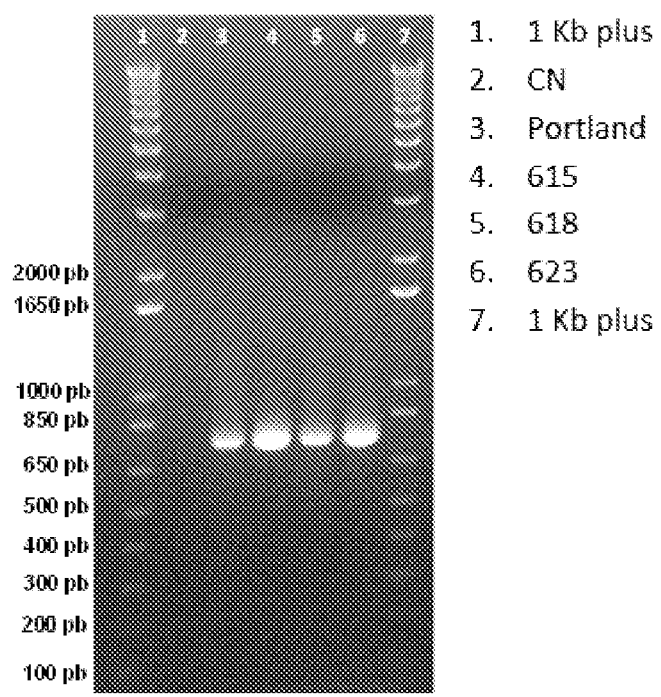
FIG. 1. PCR for the amplification of interest genes of Colombian *Giardia* strains: A. CWP1; B. Alpha giardin 7.3.
Figure 1:
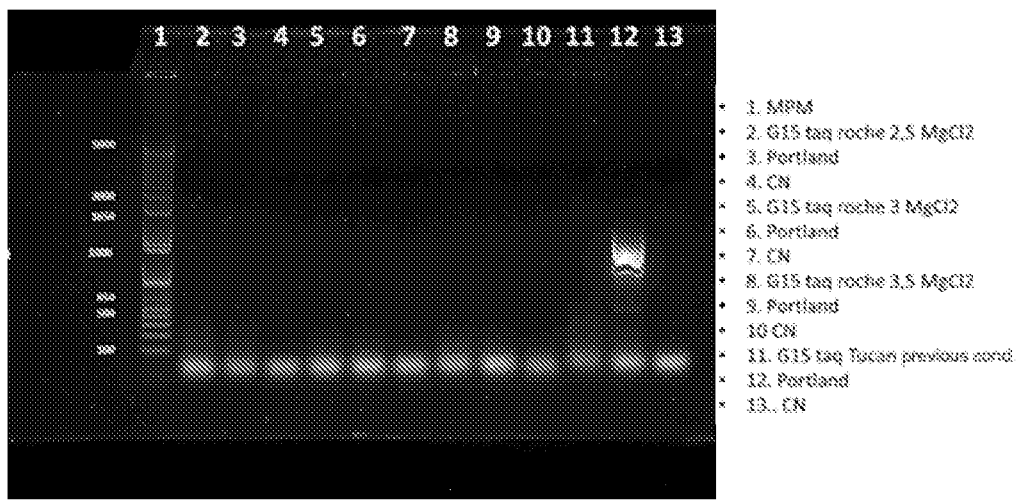

Antibodies (immunoglobulins) are protein molecules that are produced in the body in response to microorganisms or molecules (antigens) and have the ability to bind to them with a high degree of affinity and specificity. In the mammals there are five classes of immunoglobulins (IgG, IgM, IgA, IgD and IgE) and in the birds three classes (IgY, IgM and IgA). Immunoglobulins recognize relatively small components of an antigen and can cross-react with similar epitopes of other antigens, but these are generally of less specificity.

Monoclonal antibodies are generated by a single clone of B lymphocytes. Monoclonal antibodies work well when the antigens are homopolymeric, otherwise, it is necessary to develop a "pool" of monoclonal antibodies, each with different specificities, which requires much time and economic investment, since the multiple monoclonal antibodies must be identified that meet the desired specificity.

Additionally, small changes in the structure of an epitope as a consequence of a genetic polymorphism, glycosylation and denaturation may obviously affect the function of monoclonal antibodies. Although the main advantages of monoclonal antibodies are their homogeneity, consistency and monospecificity, they can limit their use in the *Giardia* detection, since it presents genetic variability as a biological factor inherent to the parasite.

Polyclonal antibodies are generated by a mixture of several B lymphocyte clones and, in general, have higher sensitivity than monoclonal antibodies. The specificity of an antibody is known as the antibody ability to recognize a specific epitope in the presence of other epitopes. Therefore, an antibody with high specificity will present a minimum of cross-reactions. In relation to protein antigens, the affinity bonds of most antibodies are influenced by their conformational structure. A change in the conformational structure is critical when using monoclonal antibodies, and of less impact when using polyclonal antibodies.

Antigens of *Giardia* isolates containing membrane and protein fractions of the parasite, may be used through immunization of rabbits and hens, to obtain anti-*Giardia* antibodies that allow detecting the parasite. Once the relevant protein antigens have been identified, it is possible to obtain them using molecular and cellular biology techniques that include the cloning of genes.

Anti-*Giardia* IgY antibodies recognize around 45 cyst and trophozoite antigens from *Giardia* isolates. Thirty-three of these are present in the cyst and the remaining 12 of 18, 20, 25, 40, 69, 74, 94, 105, 129, 200, 230 and 241 kDa belong to the *Giardia* trophozoite. The fact that *Giardia* cyst antigens are also found in the trophozoite of the parasite is an advantage given that the trophozoite stage can remain axenic in vitro, which facilitates obtaining large volumes of antigen.

In accordance with the scientific literature of the proteins recognized in cyst and trophozoite of *Giardia* isolates by IgY, anti-*Giardia* isolates may correspond to the proteins listed in Table 1:

TABLE 1

Proteins recognized by IgY anti-*Giardia* isolates

| Antigen (Protein) kDa | Location and/or function | Bibliographic reference |
|---|---|---|
| 170 | Flagellus | Rosales and Borjas, 1968 |
| 86 | Membrane | Edson and col, 1986 |
| 82 | Membrane | Einfeld and Stibbs, 1984 |
| 78 | Regulator | Reiner and Gillin, 1992 |
| 74 | Membrane | Clark and Holberton, 1986 |
| 67 | Flagellus | Crossley and Hoberton, 1986 |
| 65 | Excretion/Secretion | Rosoff Stibbs, 1986 Vinayak et al, 1993 |
| 64 | Membrane | Einfeld and Stibbs, 1984 |
| 60 | Cytoskeleton | Crossley and Holberton, 1985 |
| 56 | Membrane | Vinayak and col, 1989 |
| 52 | Membrane | Einfeld and Stibbs, 1984 |
| 49 | Membrane | Das and col, 1991 |
| 35 | Giardinas | Taylor and Wenman, 1987 |
| 24 | Membrane | Einfeld and Stibbs, 1984 |

Some of the amino acid sequences of the *Giardia* antigens that can be obtained by molecular biology techniques are shown below:

CWP1

(SEQ ID NO: 1)
MRGSHHHHHHGSMMLAFLALAGSALALTCPATQREVLVEIYDATDGANWK

TNNWLSGDSICTWTGVTCEASNNYVIALDLSDMGLTGTIPENIGCLTYLK

TLYLSNNSLAGAIPEGLCQLTNLQYLQVNSAGLTGDIPECMCDLIHLMFW

YMSDNALTGSIPTCINELQFLKELHLDCNQLSGTVPVGLMTLPYLMELYL

NCNPDLTCPDATGVQFVFKCGDVDCENCGTLPPTNCAQCFTDPDCGEYCL

TQP.

The previous sequence has 99% identity with the protein encoded by the gene GL50803_5638.

Alpha-giardin 7.3

(SEQ ID NO: 2)
MRGSHHHHHHGSMAAAKATEIKALIDAKDMDGLARSVADFDDRQRAEIYA

AFRAANGKTASEYLDALFKNGDYKDLMMIVLDDEIDVRCKLIKKAFKGGN

DERCLTDALLTTTPEVYARVKDRYHQLFGDDFESTLRKEIGSKTVWARMV

NSWLAFCRSARNNAQGDAEALKAALIGVKHPDTDTVIRLLGTTVPSEWKQ

ISEAFESIAKKTIEQALIEAYKGDDELALCCCNATLHCPARGAAYLLSLA

CQKKGDTDRCCRITGMLYDQAEQCKVLYAHYGNLAKDIRATMSKNLAEAC

CVLWHVM.

The previous sequence has 99% identity with the protein encoded by the gene GL50803_114119.

On the other hand, the expressed Kinesin 3 protein is orthologous of the gen GL50803_112846, which codes for the following amino acid sequence (SEQ ID NO: 3):

MRGSHHHHHHGSMPVTGVKVAVRVRPFNAREKREAARLCVDMPGGGKVVL

RDADAKKPDAAFVYDHAYWSHDASRPCATQDTVYADIGPSVLDNAFEGYN

YTLFAYGQTGSGKSYSMMGAPASEADAGIIPRVGRELFRRAAASPAETQV

SVSFLEIYNERLRDLLVPAAGAQELRIRQDPAAGVFVQNLSHHAVADYDA

IQRLIELGDRNRTVAATNMNATSSRSHSVFAIEVVQTAVLRNDAGEEVGR

HVKRARVSLVDLAGSERQGKTGATGDRLTEGISINKSLTTLGRVIEALAY

NTTAEGRRKPQHVPYRDSQLTYLLQPALGGNSMTCMIAAISPASTNYDES

LSTLRYADRAHQIENTVTKNESAQEKYIRELEDRVKELEALLAGGAPAGD

AGAVEPGLSDAERLELEAKIAEYDRLLKEGNQSLEEKLARAEQNRQELQD

KLKKMGLAAAFGSEITTPYISNLSSNASDNGQLIYTLCSENDLKDARPVT

VVVGADDSGPTECQCRIALVSKLGVLGEHFIISLTGKVVDSTANPIFPKV

TEATIRPLSAKGALYINGRQIAAGSTHQLRHGDRIKCGSAAQSSFYRYYD

PPARAAAVKQSLEQDYDYVEPEITYDLALREYTYYQSSGKDTAQRPIGDD

PVSKENVSVTMDDAFGITPGLDNVQTDINESFYADFGNDDERTTYEKKVH

EVLRQLYPFICEANSIAEYFCYDIRFAAQARTSISPTSLRQAARCQTIRN

MSKNHPMTKDLRADQIDDDLSGILVEILVTATAAPSKTRDRKLIRQVWAL

EKFGLRLSGMRRMYGLAMTLGKEEAVRRAHESADRDLEDDDEFPFDLEAD

IYNQTLTHLIGVGRIPLSGLLETCETDVFSVPIYDYSGKAATSIDVSLSL

LGSGYSHHGAECLACDVANLVQNESPVTTIAAYFKKAYNVPTQCCKKVHA

VIHMPWFVNPDAGRPKGKRLSVYQENEFRRRLLDMGYTFQTASSSDLSPN

PALDSTIYMDLKTSYFKQDDVLEWLRTSGTGLEVSLYGYTSAYADSLVPE

IKDSALPDPSKKKVAIVSTNIVRTQTKEDGFKEINGEQVLIIKKFIFVDQ

TKTDTGH.

Anti-*Giardia* IgG polyclonal antibodies developed in rabbit can be used to capture specific *Giardia* antigens present in fecal matter by the ELISA immunoenzymatic assay, with sensitivities and specificities ranging between 95% and 100%. These ranges may be due to some inherent physicochemical characteristics of mammalian IgG.

Since IgY polyclonal anti-microorganism antibodies decrease the probability of false positives in immunological assays, IgY polyclonal antibodies have been developed directed against parasites such as: *Echinococcus granuloses, Naegleria fowleri, Plasmodium falciparum, Sacorcystis gigantae, Toxoplasma gondii, Trypanosoma brucei, Schistosoma japonicum.*

IgY has some physicochemical characteristics that differentiate it from mammalian IgG, in such a way that the probability of giving false positives and false negatives in immunodiagnostic assays, decreases due to the elimination of nonspecific junctions. The best antibodies to detect a microorganism in clinical samples or Environmental factors using immunoassays are generally antibodies developed against the membrane of the microorganism or against protein fractions associated with it.

Purification of Anti-*Giardia* IgG and IgY Antibodies

Anti-*Giardia* polyclonal antibodies can be purified by affinity chromatography, which offers high specificity and selectivity for the isolation and purification of biomolecules. This technique is based on bio-specific interactions, thanks to which the column only absorbs the components that have affinity with the ligands coupled to the chromatographic support. When the retained compound is eluted, high levels of purity are achieved, thanks to the high selectivity of these affinity interactions.

One embodiment of the present invention corresponds to a stationary phase for purifying anti-*Giardia* IgG and IgY antibodies. The stationary phase of the invention comprises a resistant, permeable and reactive support, of matrices of polysaccharides (for example, agarose, cellulose, dextran) or synthetic matrices (e.g. glass, polyacrylamide) stable, resistant to microbial attacks, stable to changes in pH and compatible with various organic solvents. Additionally, the stationary phase of the invention comprises a mixture of two or more recombinant antigenic proteins selected from CWP1, Alpha giardin 7.3 and Kinesin 3, incorporated or dissolved in a buffer solution. Optionally, the stationary phase of the invention may comprise sodium azide in solution (0.2% w/v) to prevent contamination and thus be reused several times.

The regulating solution or buffer, for purposes of the present invention, is defined as a solution, with a certain pH, that allows resistance to pH changes when there is addition of acids or alkali. Regulatory solutions may include one, two, or more salts of phosphate, citrate, acetate (e.g. potassium metaphosphate, potassium phosphate, sodium acetate, sodium citrate anhydrous) and other salts known in the technical field to obtain such solutions.

In one embodiment of the invention, the stationary phase consists of a support comprising agarose spheres with N-hydroxy-succimide ester, which are coupled to aqueous or non-aqueous ligands in solution. This support allows the coupling, without denaturation, of two 2 or more recombinant *Giardia* antigens and guarantee their stability at −20° C. for one year and −70° C. for periods of time greater than one year The present invention also contemplates a method for purifying polyclonal anti-*Giardia* IgG and IgY antibodies, by affinity chromatography, comprising the following steps:
 a) preparing a stationary phase comprising a resistant, permeable and reactive support of polysaccharide matrices (e.g. agarose, cellulose, dextran) or synthetic matrices (e.g. glass, polyacrylamide) and a mixture of two or more recombinant antigenic proteins selected from CWP1, Alpha giardin 7.3 and Kinesin 3;
 b) blocking the free amino-reactive groups of the support with a Tris HCl buffer solution pH 8.0 after the binding of the proteins to the support, to avoid additional nonspecific binding;
 c) transferring the stationary phase obtained in step a) to a column and washing with bicarbonate buffer;
 d) adding anti-*Giardia* IgG polyclonal antibodies to the stationary phase until the gel is saturated, and in the same way, but independently, performing the process with anti-*Giardia* IgY;
 e) removing proteins or other nonspecific solutes;
 f) eluting, with an acid pH buffer solution, the specific anti-*Giardia* IgG and IgY polyclonal antibodies that had been independently added; and
 g) neutralizing.

A further embodiment of the present invention corresponds to polyclonal anti-*Giardia* IgG and IgY antibodies, purified by affinity chromatography, which specifically bind to the antigens CWP1, alpha giardin 7.3 and Kinesin 3.

Detection of *Giardia* Antigens in Samples by Immune-Enzymatic Assay

A diagnostic test refers to any method to obtain additional information on a patient's health status. The type of information acquired through the use of a diagnostic test not only includes the presence or absence of a certain disease, but also the staging of a known disease or establishing the existence of a certain condition, not necessarily pathological (Bossuyt P M, et. al., 2003).

The enzyme-linked immunosorbent assay (ELISA) is a method based on antigen-antibody reactions, incorporating an enzyme to one of these, in order to visualize the antigen-antibody binding by developing color as a product of the enzyme-substrate reaction. The ELISA assay can be used under the foundation of any of the following three modalities: i) direct ELISA; ii) indirect ELISA and iii) "sandwich" ELISA, which in turn can be direct or indirect.

The direct ELISA is used for competition and inhibition systems; the indirect ELISA has the advantage of being able to analyze a large number of samples. The direct sandwich ELISA is not recommended when it is expected to detect complex antigens and the indirect sandwich ELISA has the advantage of using different immunoglobulins from different animal species.

A further embodiment of the present invention is an in vitro diagnostic method or test for the detection of *Giardia* antigens in biological samples (e.g. feces) or environmental samples (e.g. water), comprising the following steps:
 a) adding polyclonal anti-*Giardia* antibodies IgG or anti-*Giardia* IgY (capture antibodies) in a plastic solid matrix (e.g. tubes, beads, plates or others), in a porous material of different forms, such as nitrocellulose paper, cellulose acetate, regenerated cellulose, nylon, vinylidene polyfluoride (pvdf), among others, or in fibrous materials such as fiberglass or others;
 b) incubating the matrix and washing it;
 c) blocking;
 d) incubating and washing;
 e) adding a biological or environmental sample in the solid matrix containing the anti-*Giardia* polyclonal antibodies, shaking and incubating;
 f) removing excess sample;
 g) adding purified anti-*Giardia* IgG or anti-*Giardia* IgY polyclonal antibodies;
 h) shaking, incubating and removing excess antibodies;
 i) adding a conjugate of anti-rabbit IgG or hen anti-IgY antibody bound to a reporter (enzyme or fluorescent or luminescent or chromophore molecule);
 j) shaking, incubating and removing excess conjugate;
 k) adding a detection reagent; and
 l) incubating and stopping the reaction when necessary.

The first polyclonal (capture) antibody in step (a) is that which binds to the solid matrix (as in the case of the IgY anti-*Giardia* polyclonal antibody developed in hen) and which captures the antigen to be detected (in this case, the *Giardia* antigen). The second polyclonal antibody (in this case the IgG anti-*Giardia* polyclonal antibody developed in rabbit) binds to the captured antigen and allows, with a conjugate (an anti-rabbit IgG immunoglobulin linked to an enzyme or fluorescent or luminescent or chromophore molecule), it is possible to visualize (by the development of a color product of the reaction) the *Giardia* antigen that was captured. The absence of color indicates that the sample does not contain *Giardia* antigens.

For the detection of the antigen-antibody complex reaction molecules known as reporters (markers) are used, which can be enzymatic, fluorescent, luminescent and chromophores that bind to the antigen-antibody complex, and a detection reagent that produces a detectable signal in the presence of this reporter.

The essential components for performing the diagnostic test of the invention can be combined in a single package (kit) in order to facilitate storage, transport and marketing.

This indirect sandwich ELISA can be used for the detection of *Giardia* antigen for the advantages described above and additionally because:
 i) polyclonal anti-*Giardia* IgY and anti-*Giardia* IgG antibodies do not react with each other, avoiding the idiotype-anti-idiotype recognition that generates false positives when polyclonal antibodies developed in the same animal species are used; and
 ii) avian IgY antibodies unlike mammalian IgG, does not interact with rheumatoid factors, does not activate the human complement system, does not bind to staphylococcal protein A, does not bind to the G protein or to the Fe receptors. of mammalian cells, thus decreasing the probability of giving false positives in immunological assays.

In the ELISA, the solid matrix is one of the important elements since it acts as a support immobilizing the antibodies. This solid matrix is made with different materials such as: plastic in tubes, beads, plates or others; porous materials such as nitrocellulose, cellulose acetate, regenerated cellulose, nylon, vinylidene polyfluoride (pvdf) among others, which may have different shapes and fibrous materials such as fiberglass among others (Desphande, 1996).

For the detection of the antigen-antibody complex reaction molecules known as reporters (markers) are used that can be enzymatic, fluorescent, luminescent and chromophoric that bind to the antigen-antibody complex and a detection reagent that produces a detectable signal in the presence of this reporter.

In a further embodiment, the present invention contemplates a diagnostic kit comprising a solid matrix, polyclonal anti-*Giardia* IgG antibodies, polyclonal anti-*Giardia* IgY antibodies, conjugate and a detection reagent.

The following examples illustrate the invention, without the inventive concept being restricted thereto:

EXAMPLES

Example 1. Identification of *Giardia* Proteins Recognized by Polyclonal Anti-*Giardia* IgG Antibodies and Polyclonal Anti-*Giardia* IgY Antibodies from Colombian Isolates 1.1 Isolation of *Giardia* from Human Fecal Matter.

Identification of fecal *Giardia* cysts and isolation of cysts by purification thereof:

Parasitological diagnosis was made in human fecal matter to determine the presence or absence of cysts of *Giardia* and other intestinal parasites by the direct method in saline and lugol (Melvin and Brooke, 1980) and the method of formaldehyde-ether concentration (Ridley et al. Hawgood, 1956). The purification of *Giardia* cysts from fecal matter was performed using gradients of sucrose and Percoll (Sauch, 1984).

Eluates of human fecal matter (coproantigen): Fecal eluates stored in the Samples Bank of the Parasitology Group of the National Institute of Health were defrosted. Detection of *Giardia* antigen in human fecal eluates was performed by ELISA using antibodies polyclonal anti-*Giardia* IgG and polyclonal antibodies anti-*Giardia* IgY, developed in rabbit and hen, respectively.

1.2 Gerbil—Animal Model for Studies of Giardiosis.

Gerbils Quarantine and Maintenance:

Gerbils were quarantined and maintained in the Bioterium of the National Health Institute (Bogota, Colombia), following the protocols and procedures established in the ABSL2 of the INS, the norms established in the Guide for the care and use of laboratory animals, 2010 and those of the Council of International Organizations of Medical Sciences (CIOMS), 1996.

Prophylaxis and Infection with *Giardia* Cysts to Gerbils:

Ten gerbils were given Secnidazole (Secnidal®) in a dose of 0.2 g/Gerbil in a single dose. Eight gerbils were experimentally inoculated orally with 5×10 cysts of Colombian *Giardia* isolates (positive controls) by intubation with a naso-gastric tube, impregnated with lidocaine, guaranteeing that the specimens would only be infected with *Giardia*. The two remaining gerbils (negative controls) were not infected with the parasite.

Diagnosis of *Giardia* in Gerbil's Feces:

The presence or absence of *Giardia* cysts or trophozoites was established in the fecal matter of the gerbils infected with the parasite, as well as of the uninfected, by the direct method in saline and lugol (Melvin and Brooke, 1980) and the formalin-ether concentration method (Ridley and Hawgood, 1956).

Preparation of fecal matter eluent (coproantigen) from Germs not infected (negative controls), infected (positive controls) and gerbils naturally infected with *Trichomonas hominis* (cross-reaction):

The feces of each of the infected gerbils were collected independently, not infected with cysts of Colombian isolates of *Giardia*, daily and for 30 consecutive days (Arévalo et al., 2005). Approximately 1 gram of fecal matter was homogenized in 10 milliliters of phosphate buffer saline (PBS) pH 7.2. The homogenate was filtered through of double gauze allowing the sedimentation of large particles present in the feces for 20 minutes at room temperature.

The coproantigen was stored at −20° C. (Green, 1985) and defrosted at the time of detecting *Giardia* antigen by ELISA using polyclonal anti-*Giardia* IgG antibodies and polyclonal anti-*Giardia* IgY antibodies, developed in rabbit and hen, respectively.

Isolation of *Giardia* Trophozoites from the Small Intestine of Gerbils Infected with the Parasite:

Euthanasia was performed on the gerbils using $CO_2$. The small intestine of the specimens was resected under aseptic and biosecurity conditions (Arévalo, 1999).

In Vitro Maintenance of *Giardia* Trophozoites:

TYI-S-33 culture medium supplemented with bile and antibiotics (TYI-S-33-B) was used and *Giardia* trophozoites were incubated at 35° C. (Keister, 1983).

Preparation of *Giardia* Antigen:

*Giardia* trophozoites isolated from the small intestine of gerbils were frozen at −196° C., defrosted at 4° C. and sonicated at 20 kHz. The supernatant (antigen) was centrifuged and preserved and the protein concentration was determined by the Bradford method.

1.3 Identification of *Giardia* Antigens with Diagnostic Potential Through in Silico Analysis and Review of Scientific Literature.

A review of scientific literature was carried out to identify publications that used the experimental *Giardia* model, in which antigens are identified or proposed as candidates for the immunodiagnosis of giardiasis. Moreover, a bio-informatic analysis was made considering criteria such as molecular mass or excretion/secretion proteins.

These criteria were used as the first filter to search for proteins of interest in the *Giardia* genome database that is available online at http://giardiadb.org/giardiadb, then criteria such as: selection of surface proteins, the prediction of immunogenic B epitopes; located on the surface of the molecule at accessible sites for the free antibody.

Finally, two proteins with potential usefulness for immunodiagnosis were selected; the protein CWP1 of the wall of the cyst (GL50803_5638) and the alpha giardin 7.3 (GL50803_114787). The sequence of the respective genes was downloaded for the strains of *Giardia* with sequenced genome and with these we proceeded to make multiple alignment of sequences in search of conserved regions to design primers that allowed the amplification of these genes in Colombian strains of *Giardia*.

1.4 Amplification of the Genes of Interest.

To amplify the genes of interest, DNA was extracted from 3 strains of *Giardia* from different geographical regions of Colombia (MHOM/Co/99/GI-15 from Tarapacá Amazonas, MHOM/Co/99/GI-18 from Garagoa Boyacá, MHOM/Co/99/GI-23 Popayán Cauca). The PCR was done using the CloneAmp™ HiFi PCR Premix kit following the manufacturer's recommendations.

The amplification products were separated on 1% agarose gels, TAE IX, stained with GelRed™ 1/10,000 and visualized with ultraviolet light in a GelDoc™ XR+(Image Lab™ Software) (FIG. 1). The fragments of the expected size were cut out of the gel, purified using the Zymoclean™ Gel DNA Recovery kit and quantified in a NanoDrop 2000.

Figure 2:
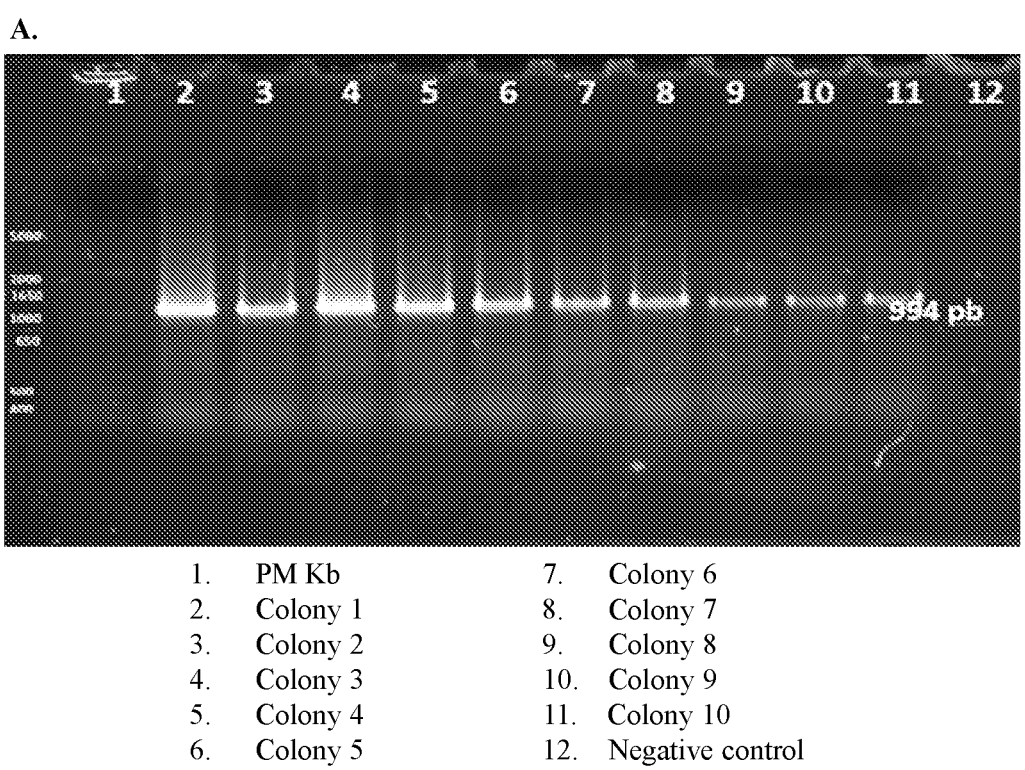
FIG. 2. Detection of carrier colonies of the recombinant plasmid—Colony PCR: A. CWP1; B. Alpha giardin 7.3.
Figure 2:
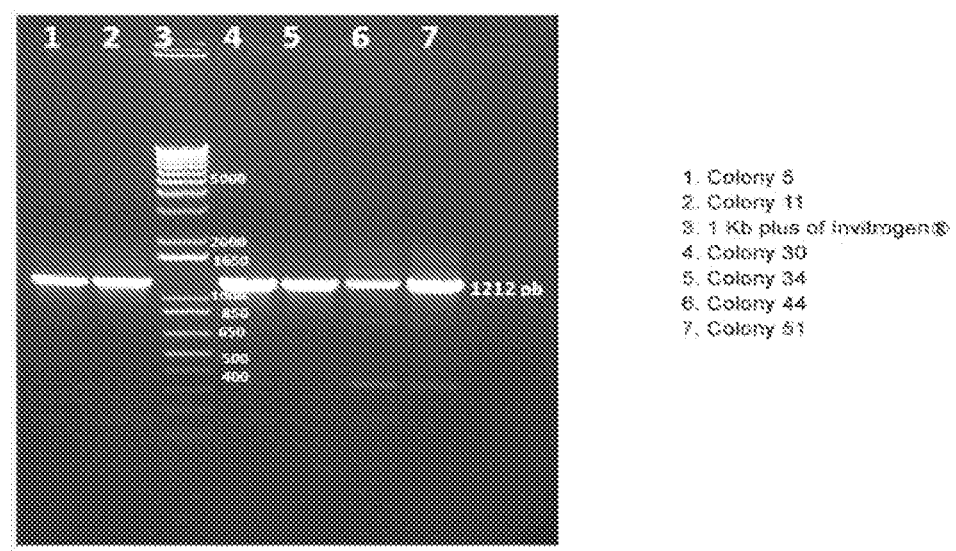

The fragments were cloned directly into an expression plasmid using the In-Fusion® HD Cloning kit following the manufacturer's recommendations. With these plasmids, *E. coli* XL1-Blue cells were transformed and plated into Luria Bertani (LB) agar boxes with tetracycline/ampicillin. To detect the carrier colonies of recombinant plasmid, a colony PCR was developed using primers that align on the expression plasmid (FIG. 2).

Plasmid DNA was extracted from the colonies carrying the recombinant plasmid and sequenced in the DNA Sequencing Laboratory of the Universidad de los Andes (Bogotá, Colombia). The sequences were visualized and edited using the BioEdit program. To confirm the identity of the sequences, a BLAST (Basic Local Alignment Search Tool) was made at the NCBI (National Center for Biotechnology Information).

1.5 Obtaining the Recombinant Proteins

Once the identity of the gene of interest within the expression plasmid was confirmed, *E. coli* MI 5 cells were transformed with each plasmid and induction tests were carried out under optimum conditions of optical density of the culture. non-induced, IPTG concentration and induction temperature (Table 2). Bacterial culture was staggered, under adequate conditions, in order to mass produce the proteins of interest.

TABLE 2

Induction conditions of each of the recombinant proteins

| Protein Conditions | CWP1 | Alpha Giardina 7.3 | Kinesin |
|---|---|---|---|
| Optical Density | 0.3 | 0.3 | 0.8 |
| IPTG concentration | 0.5 mM | 0.5 mM | 0.5 mM |
| Incubation Temperature | 25° C. | 18° C. | 18° C. |
| Time | 18 hours | 18 hours | 18 hours |

Figure 3:
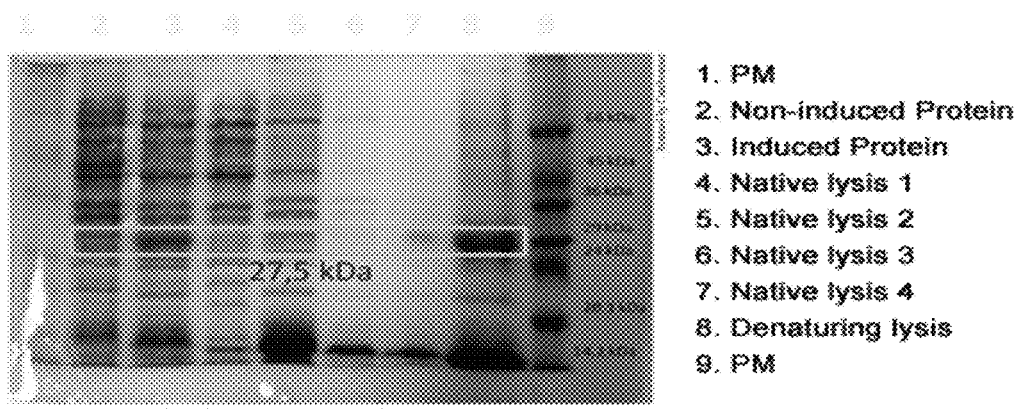
FIG. 3. Lysed affinity purification of the native recombinant protein in Nickel resin (Ni+2): A. CWP1; B. Alpha giardin 7.3.
Figure 3:
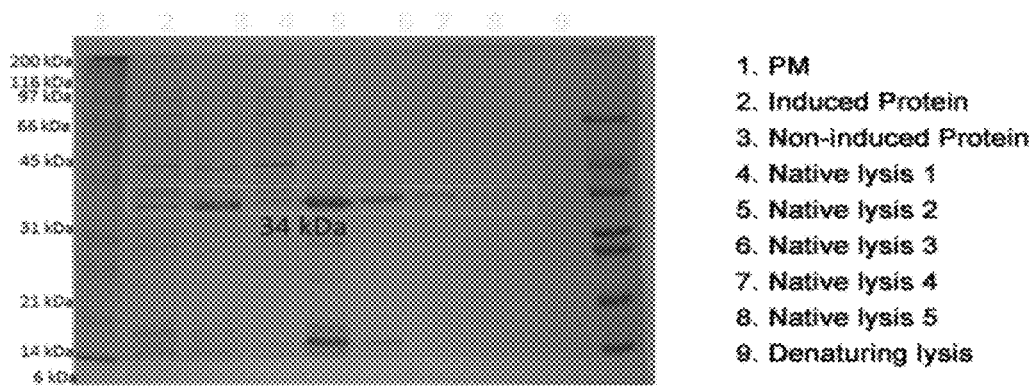

The extraction of the recombinant protein in its native form was performed using a lysis buffer containing 0.1×PBS and 0.1% triton X-100, sonicating in Ultrasonic processor GEX 130 with amplitude of 65% and in 3 cycles of 20 seconds The used ones of the native recombinant protein were purified by affinity in Nickel resin (Ni+2) (Ni2+-NTA-Agarose resin columns (QIAGEN, Inc., Hilden, Germany), FIG. 3.

Figure 4:
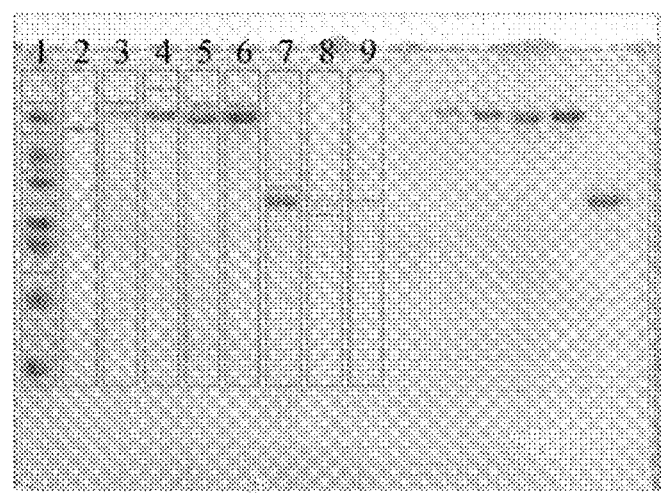
FIG. 4. Concentration of the recovered protein.
Figure 4:
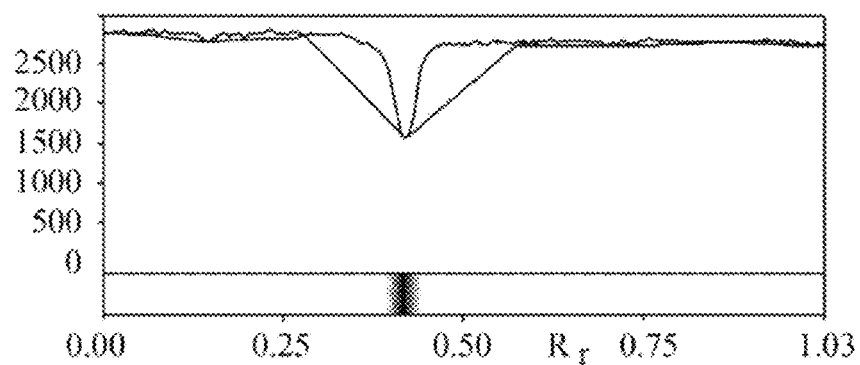

The recombinant protein purified by affinity was separated by SDS-PAGE. In order to obtain a protein free of salts or compounds that could interfere with subsequent methodologies, the next step was to dialyze the protein in PBS IX buffer with 1% glycerol at 4° C. for 4 hours. Once the dialysis process was concluded, the protein was quantified in SDS-PAGE gel using a standard curve of known concentrations of bovine serum albumin (BSA), the documented image of this gel was used to develop a densitometry analysis that allowed to know the concentration of the recovered protein (FIG. 4).

Figure 5:
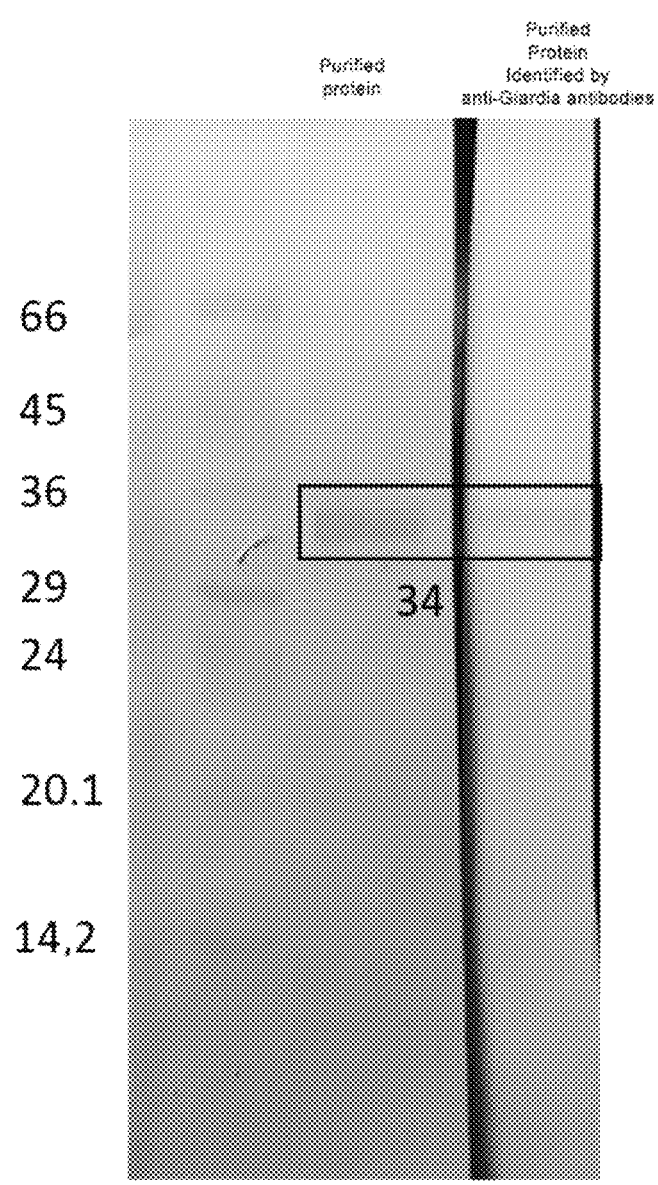
FIG. 5. Western Blot: specific recognition of a single band of 34.2 kDa for the Alpha giardin –7.3.
Figure 6:
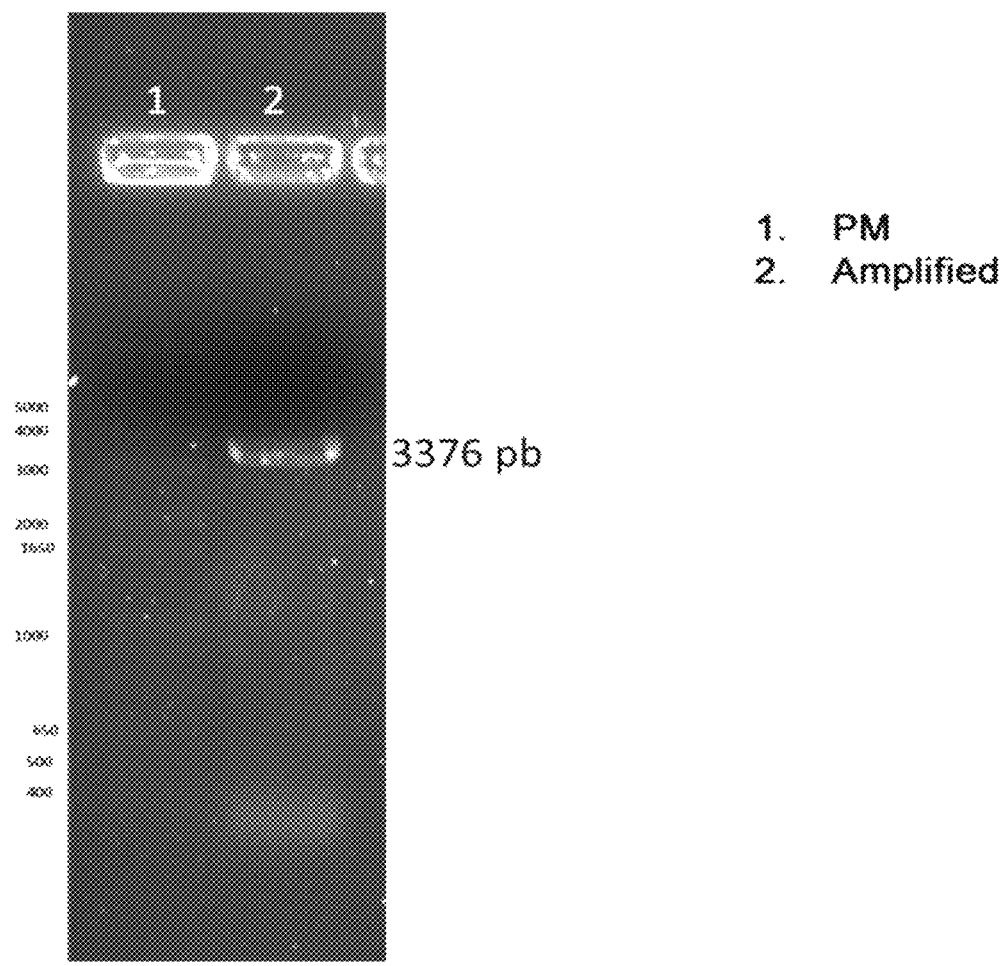
FIG. 6. PCR amplification of the Kinesin 3 gene.
Figure 7:
FIG. 7. PCR colony of Kinesin 3.
Figure 8:
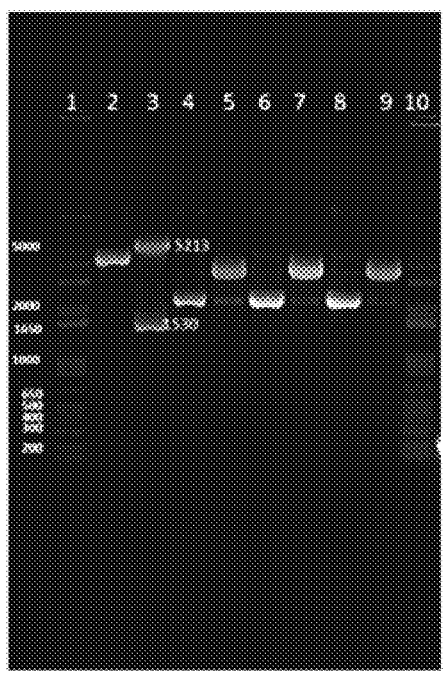
FIG. 8. Screening of colonies by using restriction enzyme (PstI) to identify the plasmids carrying the fragment of expected size for Kinesin 3.
Figure 9:
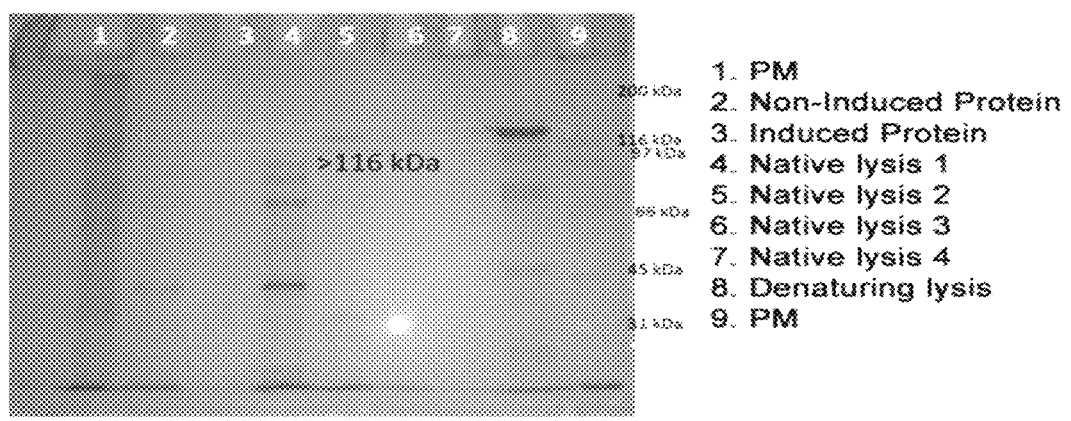
FIG. 9. Purification scheme for Kinesin 3.
Figure 10:
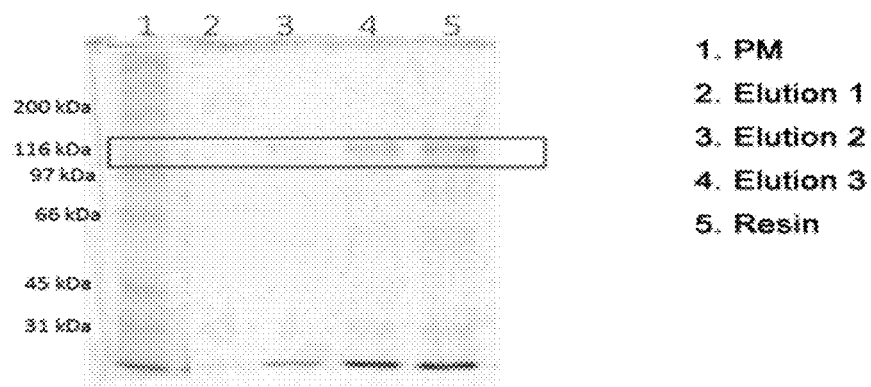
FIG. 10. SDS-PAGE gel: purification of Kinesin 3 by affinity chromatography on nickel-loaded resin.

In order to confirm that the recovered protein is indeed recognized by the polyclonal IgG antibodies against Colombian isolates of *Giardia*, a Western Blot was made, which revealed the specific recognition of a single band of the expected size (27.5 kDa for the CWP1 protein and 34.2 kDa for the alpha-giardin 7.3) (FIG. 5).

1.6 In Vitro Detection of *Giardia* Antigens with Potential for Immunodiagnosis, Through Immunoprecipitation and Mass Spectrometry, Universal Methodologies.

The antibodies developed in rabbit against a pool of 25 Colombian isolates of *Giardia*, were united to magnetic microbeads coated with protein A/G and this complex was used to capture proteins present in the Used of *Giardia* trophozoites by the universal immunoprecipitation technique (IP).

Simultaneously, the same process was developed using pre-immune antibody, which was taken as the non-specificity control. After several washes, the retained protein was eluted and LC/MS/MS mass spectrometry analysis was performed (universal methodology). In this way it was possible to identify 30 proteins of *Giardia*, of which only 7 proteins remained, when eliminating those that appeared in the elution of the pre-immune serum. When making a functional analysis of the remaining proteins, a structural protein was selected, which was Kinesin 3 (GL50803_112846). The design of primers, PCR amplification, cloning and expression of this protein was done in the same way as for the two previous proteins (FIGS. 6-10).

Example 2. Purification of Polyclonal Anti-*Giardia* IgG Antibodies and Anti-*Giardia* IgY Polyclonal Antibodies 2.1 Stationary Phase Affigel 10® is a commercial stationary phase of BIO-RAD® composed of agarose spheres with N-hydroxy-succimide ester that are coupled to aqueous or non-aqueous ligands in solution. The recombinant *Giardia* antigens developed in the National Institute of Health obtained according to Example 1 were coupled to the Affigel, without denaturation.

The affi-gel 10® was uniformly homogenized, one milliliter of it was removed and washed with five volumes of isopropanol refrigerated at 4° C. 0.5 ml of a solution that may contain the combination of two or three recombinant antigens or total parasite antigens dissolved in phosphate buffer in a final concentration of 30 mg, was stirred at 18° C. for one hour to obtain a uniform suspension, the active groups were blocked by adding 0.1 ml of 1M ethanolamine HCl (pH 8.0) for one hour, and transferred to a Biorad® Econo-Pack column of 10 ml capacity. Finally, it was washed with bicarbonate buffer until the obtained gel was free of reagents, which was detected by optical density at a wavelength of 280 nm.

2.2 Polyclonal Anti-*Giardia* IgG Antibodies Developed in Rabbit and Polyclonal Anti-*Giardia* IgY Antibodies Developed in Hen IgY anti-*Giardia* polyclonal antibodies present in egg yolks were developed in hens immunized with parasite trophozoites, in previous studies, and egg yolks stored at −20° C. The egg yolks were defrosted at 4° C. and mixed with sterile distilled water in a ratio of 1:9 v/v. It was filtered through sterile double gauze and the filtrate was adjusted to pH 7.0 with 0.1N NaOH (Garcia et al., 2005). IgG anti-*Giardia* polyclonal antibodies present in serum were developed in rabbit and previously purified by precipitation sequential with caprylic acid and ammonium sulfate, in previous studies, and subsequently stored at −20° C. (Duque et al., 2002). They were defrosted at 4° C. and purified by affinity chromatography.

2.3 Purification of Polyclonal Anti-*Giardia* IgG Antibodies and Anti-*Giardia* IY Polyclonal Antibodies, by Affinity Chromatography.

IgG and IgY anti-*Giardia* polyclonal antibodies were added, independently, in the upper part of the column until the gel was saturated, proteins or other nonspecific solutes were removed with 1M sodium chloride (NaCl), polyclonal IgG and IgY antibodies were eluted. anti-*Giardia*, independently, with 1M propionic acid and neutralized with a base (Bio-Rad®).

2.4 Determination of the Biological Activity of Polyclonal Antibodies IgG and IgY Anti-*Giardia*.

The biological activity of polyclonal antibodies IgG and IgY anti-*Giardia* was determined, independently, by Western Blot. The recognition of *Giardia* trophozoite antigens was performed by the procedure described by Laemmli, 1970 and Towbin et al, 1979.

*Giardia* trophozoite proteins were separated by polyacrylamide gel electrophoresis under denaturant conditions using a 12.5% polyacrylamide gel separator. The proteins were transferred to a nitrocellulose membrane (MNC) at 4° C./200 mA/130 volts/26 watts for 2 hours and the transfer of the proteins was verified by coloring the MNC with Ponceau S. red.

The MNC was blocked with 4% skim milk dissolved in PBS-0.1% Tween 20 (PBS-T) at 18° C. for one hour, and washed three times with PBS-T, for five minutes each time. IgG and IgY anti-*Giardia* polyclonal antibody was added to the MNC, independently, at a 1:400 dilution, incubated at 18° C. for 18 hours and washed as described above.

The MNC was incubated at 18° C. for 1 hour with a 1:10,000 dilution, independently, of anti-IgG (Biorad®) and anti-IgY (Promega®) both bound to alkaline phosphatase. The MNC was washed twice with PBS-T and once with Tris-NaCl-MgCl buffer. The reaction was revealed with 5-bromo-4-chloro-3-indole phosphate (BCIP) and nitrotetrazolium blue (NBT). The reaction was stopped using a buffer solution of the enzymatic reaction (sodium chloride, potassium chloride, potassium monobasic phosphate, sodium dibasic phosphate, ethylene diamine tetraacetic acid (EDTA).

Example 3. Development of the Indirect Sandwich ELISA for Detection of *Giardia* Antigen in Eluate of Gerbil Feces, Animal Model for Studies of Giardiosis 3.1 Enzyme Immunoassay Indirect Sandwich ELISA:

Polyclonal anti-*Giardia* IgG antibodies developed in rabbit were used, as the first capture of *Giardia* antigen and polyclonal anti-*Giardia* IgY antibodies, developed in hens, as the second capturer for the detection of the parasite in fecal matter of gerbil. Moreover, polyclonal anti-*Giardia* IgY antibodies, developed in hen, as the first capture of *Giardia* antigen and polyclonal anti-*Giardia* IgG antibodies, developed in rabbit, as the second capturer for the detection of the parasite in fecal matter of Gerbil.

The optimal concentrations of the biologics for the ELISA were determined as the optimal concentration of coproantigen, polyclonal anti-*Giardia* IgG antibody, polyclonal anti-*Giardia* IgY antibody and commercial conjugates (anti-rabbit IgG and hen anti-IgY both bound to a reporter) following the guidelines established by Voller et al., 1976 and McLaren et al., 1981).

3.2 Standardization of Optimal Biological Concentrations

Polystyrene plates were used (Ref: 95029380 Combiplate 12×25 flat bottom universal 250/crt, Labsystem®). Dilutions of anti-polyclonal antibody were made *Giardia* IgG and anti-*Giardia* IgY polyclonal antibody, independently, in final concentration of 0.1, 0.5, 1, 2, 5, 10, 20, 40, 80, 160 and 320 µg/ml in 0.05M buffer of carbonate/bicarbonate pH 9.6, 100 µl of each of the dilutions was added in triplicate in the wells of the plates and shaken once for five minutes or as an alternative to three rpm for two minutes using a plate mixer (Titer plate Shaker, Lab Line Instruments, Inc.) in order to optimize the adsorption of polyclonal antibodies to the plates. These were incubated in a humid chamber at 4° C. for 18 hours.

The plates were washed three times consecutively with 0.15M phosphate buffer, pH 7.4 plus 0.05% Tween 20 (PBS-T) for five minutes each time and alternatively using the automatic plate washer (Wellwash 4 MK 2 Thermo Labsystems®) four times for two minutes each time. The plates were blocked with 1% bovine serum albumin by adding 1000 in each well and shaken once for five minutes and as an alternative to three rpm for two minutes. The plates were incubated in a humid chamber at 18° C. for one hour. The excess bovine serum albumin was removed by washing three consecutive times with PBS-T for five minutes each time and as an alternative using the automatic plate washer four times for two minutes each time.

A 1:1 dilution of 1% bovine serum albumin and fecal eluates was performed, independently, without the presence of *Giardia* (negative samples), with the presence of *Giardia*, coproantigen, (positive samples) and with the presence of *Trichomonas hominis*, intestinal parasite different from *Giardia*, (cross-reactive samples) and 100 µl of this was added to each of the wells containing polyclonal anti-*Giardia* IgG antibodies or polyclonal anti-*Giardia* IgY antibodies, independently, adsorbed on the plates and these were shaken once for five minutes and, as an alternative, at three rpm for two minutes.

Plates were incubated in a humid chamber at 37° C. for one hour. Excess eluate was removed from fecal material by washing three consecutive times with PBS-T for five minutes each time and as an alternative using the automatic plate washer four times for two minutes each time.

Dilutions of polyclonal anti-*Giardia* IgG and IgY antibodies, independently, in final concentrations of 0.1, 0.5, 1, 2, 5, 10, 20, 40, 80, 160 and 320 µg/ml in PBS-T were made, and 100 µl of each of the dilutions was added in triplicate in the wells of the plates. The plates were shaken once for five minutes or, alternatively, at three rpm for two minutes in order to homogenize the reaction. Plates were incubated in a humid chamber at 37° C. for one hour. Excess polyclonal antibodies were removed three consecutive times with PBS-T for five minutes each time and, alternatively, using the plate washer four times for two minutes each time.

PBS-T dilutions of goat anti-rabbit IgG conjugate (Biorad®) and goat anti-hen IgG conjugate (Promega®) were both prepared, both bound to the enzyme alkaline phosphatase in dilutions with final concentration of 1:500, 1:1000; 1:2000; 1:5000 and 1:10,000. 100 µl were added to each well of the plates, these were shaken once for five minutes and, alternatively, at three rpm for two minutes in order to homogenize the reaction.

Plates were incubated in a humid chamber at 37° C. for one hour. The excess conjugate was removed by washing three consecutive times with PBS-T for five minutes each time and, alternatively, using the plate washer four times for two minutes each time. 1000 of substrate (p-nitrophenylphosphate) was added at a concentration of 1 mg/ml of 0.1M diethanolamine buffer solution, pH 9.8.

Plates were incubated at 18° C. for 30 minutes. The enzyme-substrate reaction was stopped with 25 µl of 3N sodium hydroxide (NaOH). The optical density value was determined at a wavelength of 405 nm in a Multiscan EX®.

3.3 Validation (Determination of Diagnostic Discrimination) of the Indirect Sandwich ELISA for the Detection of *Giardia* Antigen in Eluted Feces of Gerbil, Animal Model for Studies of Giardiosis.

Fecal Samples (Eluates of Fecal Matter) from Gerbil:

The minimum sample size needed in Epidat 2 was calculated based on the following assumptions: A confidence level of 95%, a difference of the sample means it does not exceed the difference of true means in a percentage greater than 12%, a deviation standard of the optical density of the population of infected gerbils of 0.40 and one standard deviation of the optical density of the population of non-infected gerbils of 0.10.

In accordance with the above, the total fecal sample size for the evaluation of the immunoenzymatic test for fecal antigen detection was 92 samples (46 fecal without and 46 with the presence of *Giardia*, positive and negative samples, respectively). Additionally, 13 fecal samples from Gerbil naturally infected with *Trichomonas hominis* (cross-reaction) were evaluated.

3.4 Diagnostic Discrimination

Once the concentrations of the biologics had been determined to perform the ELISA, we proceeded to detect *Giardia* antigen in the eluted feces of infected and uninfected gerbils by ELISA to establish the absorbance value that allowed to discriminate between presence and absence of *Giardia* antigen (Kurstak, 1985). The ELISA was evaluated by determining the parameters of: sensitivity (S), specificity (E), positive predictive value (PPV) and negative predictive value (NPV) and concordance (Kappa index), with their 95% confidence intervals using a table of 2×2 contingency (Griner et al., 1981).

Example 4. Detection of *Giardia* Antigen in Human Fecal Eluates Using the ELISA Developed in Gerbil 4.1 Sample of Human Feces (Eluates of Fecal Material):

Eluates of human fecal matter were used with presence of *Giardia* (positive samples), absence of the parasite (negative samples) and presence of other parasites. intestinal (cross-reaction), stored in the Samples Bank of the Parasitology Group of the National Institute of Health (Bogota, Colombia).

The minimum sample size needed was calculated in Epidat 2 based on the following assumptions: A confidence level of 95%, a difference of the sample means that did not exceed the difference of true means in a percentage greater than 12%, a deviation standard of optical density of the human population infected with *Giardia* of 0.40 and one standard deviation of the optical density of the human population not infected with the parasite of 0.20.

According to the above, the total fecal sample size for the evaluation of the immunoenzymatic test for antigen detection in human fecal matter was 92 samples: 46 fecal matter with presence of *Giardia* (positive samples) and 46 feces with absence of the parasite (negative samples). Additionally, 39 samples of human fecal matter infected with other intestinal parasites different from *Giardia* (Cross Reaction) were evaluated.

TABLE 3

Intestinal parasites identified in human fecal matter

| Identification of intestinal parasites | Number of human feces |
|---|---|
| Absence of *Giardia duodenalis* and other intestinal parasites | 46 |
| *Giardia duodenalis* | 46 |
| Intestinal parasites other than *Giardia duodenalis*: | 39 |
| Complex *Entamoeba histolytica*/*Entamoeba dispar* | 1 |
| *Entamoeba coli* | 7 |
| *Endolimax nana* | 1 |
| *Chilomastix mesnili* | 1 |
| *Trichomonas hominis* | 1 |
| *Blastocystis hominis* | 1 |
| *Strongyloides stercoralis* | 1 |
| *Uncinaria* | 1 |
| *Entamoeba coli*, *Chilomastix mesnili* | 6 |
| *Endolimax nana*, *Chilomastix mesniii* | 2 |
| *Entamoeba coli*, *Endolimax nana* | 2 |
| *Entamoeba coli*, *Chilomastix mesnili* | 1 |
| *Chilomastix mesnili*, *Blastocystis hominis* | 1 |
| *Chilomastix mesnili*, *Trichuris trichiura* | 1 |
| *Entamoeba coli*, *Trichuris trichiura* | 1 |
| *Entamoeba coli*, *Uncinaria*, *Trichuris trichiura*, *Hymenolepis diminuta* | 1 |
| *Entamoeba coli*, *Endolimax nana*, *Chilomastix mesnilii* | 6 |
| *Entamoeba coli*, *Iodamoeba bustchlii*, *Blastocystis hominis* | 1 |
| *Entamoeba coli*, *Endolimax nana*, *Chilomastix mesnili*, *Blastocystis hominis* | 2 |

4.2 Diagnostic Discrimination for the Detection of *Giardia* in Human Fecal Fluid Eluates by Means of Indirect Sandwich ELISA:

The optimal concentrations of the determined biologicals were used for the detection of *Giardia* antigen in gerbil feces, animal model for studies of giardiosis. Polystyrene plates were used (Ref: 95029380 Combiplate 12×25 flat bottom universal 250/crt, Labsystem®).

Dilutions of anti-*Giardia* IgG and IgY polyclonal antibody were made, independently, in a final concentration of 10 µg/ml in 0.05M carbonate/bicarbonate buffer 9.6,6, 100 µl of each of the dilutions were added in triplicate. in the wells of the plates and shaken once for five minutes and as an alternative to three rpm for two minutes using a plate mixer (Titer plate Shaker, Lab Line Instruments, Inc.) in order to optimize the adsorption of antibodies polyclonal to the plates.

These were incubated in a humid chamber at 4° C. for 18 hours. The plates were washed three times consecutively with 0.15M phosphate buffer, pH: 7.4 plus 0.05% Tween 20 (PBS-T) for five minutes each time and, alternatively, using the automatic plate washer. (Wellwash 4 MK 2 Thermo Labsystems®) four times for two minutes each time.

Plates were blocked with 1% bovine serum albumin by adding 100 µl in each well and shaken once for five minutes and, alternatively, at three rpm for two minutes. The plates were incubated in a humid chamber at 18° C. for one hour. The excess bovine serum albumin was removed by washing three consecutive times with PBS-T for five minutes each time and as an alternative using the automatic plate washer four times for two minutes each time.

A 1:1 dilution of 1% bovine serum albumin and fecal eluate was performed, independently, without the presence of *Giardia* (negative samples), with the presence of *Giardia*, coproantigen, (positive samples) and with the presence of other intestinal parasites. different from *Giardia*, (cross-reactive samples) and 100 μl thereof was added in each of the wells containing polyclonal antibodies IgG or IgY anti-*Giardia*, independently, adsorbed on the plates and these were shaken once for five minutes and, alternatively, at 3 rpm for two minutes.

Plates were incubated in a humid chamber at 37° C. for one hour. Excess eluate was removed from fecal material by washing three consecutive times with PBS-T for five minutes each time and, alternatively, using the automatic plate washer four times for two minutes each time. Dilutions of anti-*Giardia* IgG and IgY polyclonal antibody in final concentration of 10 μg/ml in PBS-T were made and 100 μl of each of the dilutions was added in triplicate in the wells of the plates.

The plates were shaken once for five minutes and as an alternative to three rpm for two minutes in order to homogenize the reaction. Plates were incubated in a humid chamber at 37° C. for one hour. Excess antibody was removed in a polyclonal fashion three consecutive times with PBS-T for five minutes each time and, alternatively, using the plate washer four times for two minutes each time.

Dilutions, in PBS-T, of the goat anti-rabbit IgG conjugate (Biorad®) bound to the alkaline phosphatase enzyme were prepared in dilution with a final concentration of 1:1000. 100 μl was added to each well of the plates, they stir once for five minutes and, alternatively, at 3 rpm for two minutes in order to homogenize the reaction.

Plates were incubated in a humid chamber at 37° C. for one hour. The excess conjugate was removed by washing three consecutive times with PBS-T for five minutes each time or, alternatively, using the plate washer four times for two minutes each time. 100 μl of substrate (p-nitrophenylphosphate) was added at a concentration of 1 mg/ml of 0.1 M diethanolamine buffer, pH 9.8. The plates were incubated at 18° C. for 30 minutes and the enzyme-substrate reaction was stopped with 25 μl of 3N sodium hydroxide (NaOH). The optical density value was determined at a wavelength of 405 nm in a MultiscanEX®.

Example 5. Results of the Infection of Gerbils with Cysts of Colombian Isolates of *Giardia*

Infection with Cysts of Colombian Isolates of *Giardia*

The infection of the specimens was achieved with the inoculation of $5 \times 10^3$ cysts of *Giardia*/ml and the corroborated infection course, daily, during 30 consecutive days by means of the parasitological diagnosis allowed to identify the presence of *Giardia* cysts or trophozoites in the fecal of Gerbils. Thus, although no cysts of the parasite were observed in some feces of infected gerbils, it was known that parasite antigen existed in their feces due to the experimental infection with *Giardia* that had been performed on the gerbils.

Figure 11:
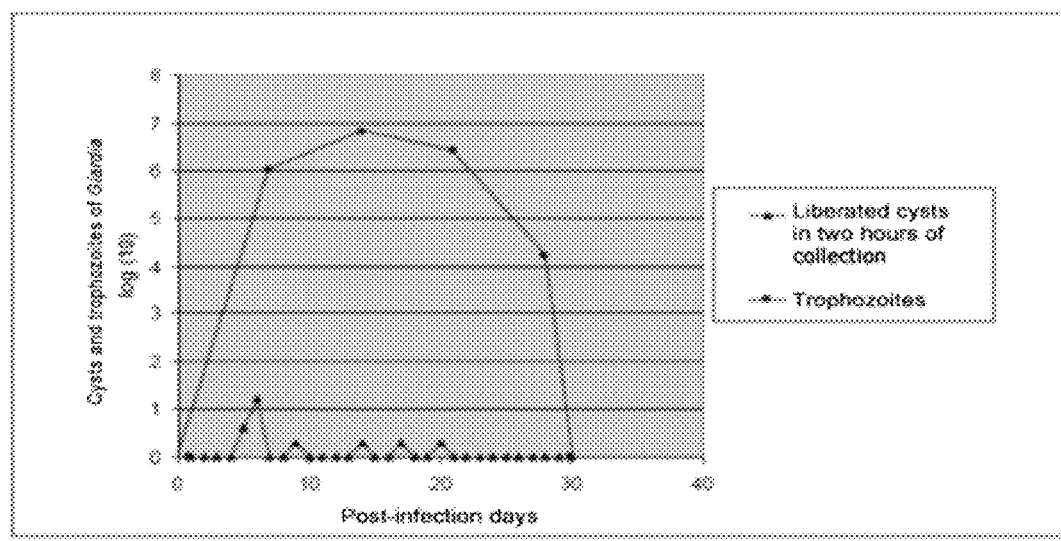
FIG. 11. Pattern of excretion of cysts and trophozoites from Colombian *Giardia* isolates during experimental infection in Gerbils (animal model for studies of giardiosis).

The course of the infection showed an intermittent pattern of parasite cysts excretion with absence of these on days 1, 2, 3, 4, 7, 8, 10, 11, 12, 13, 15, 16, 18, 19 and from day 21 to 30 post-infection and with constant presence of *Giardia* cysts during days 5, 6, 9, 14, 17 and 20 post-infection (FIG. 11).) During this period, the average concentration of Parasite cysts varied within the range of 2 (log 10:0.30) to 17 (log 10:1.23) cysts released during two hours of collection.

Due to the large difference in the orders of magnitude between the number of cysts and the number of trophozoites obtained in the collection, and in order to graphically visualize the release behavior of these, the logarithmic transformation of the data was used. The number of *Giardia* trophozoites recovered from the small intestine was different in each of the observations conducted with a range between 15,000 (log 10:4.2) and 6,577,778 (log 10:6,8) trophozoites/ml.

Isolation of *Giardia* Trophozoites from the Small Intestine of Gerbils and In Vitro Maintenance of Parasite Trophozoites

*Giardia* trophozoites were obtained at 7, 14, 21, 28 and 30 post-infection days of each of the small resected intestines of each of the gerbils that had been previously infected with the parasite. The small intestine resection of gerbils infected with *Giardia* allowed to isolate trophozoites from the parasite, maintain them in vitro, obtain mass culture of these and prepare *Giardia* trophozoite antigen at a concentration of 30 mg/ml. *Giardia* trophozoites obtained from the dried intestines of gerbils infected with the parasite were maintained in vitro, increasing the population of the parasite to a number of $1 \times 10^6$ trophozoites/ml.

Utility of IgY Anti-*Giardia* from Colombian Isolates to Detect Antigen of the Parasite in Human Fecal Matter and Gerbil (Animal Model for Studies of Giardiosis)

Preparation of *Giardia* trophozoite antigen: The *Giardia* antigen was prepared according to the proposed methodology and the protein concentration determined by the Bradford method was 1.2 mg/ml.

Example 6. Polyclonal Anti-*Giardia* Antibodies IgG and IgY

Purification by affinity chromatography of polyclonal IgG and anti-*Giardia* IgY antibodies. Anti-*Giardia* IgG and IgY concentrations of 5 mg/ml and 25 mg/ml were obtained, respectively.

Figure 12:
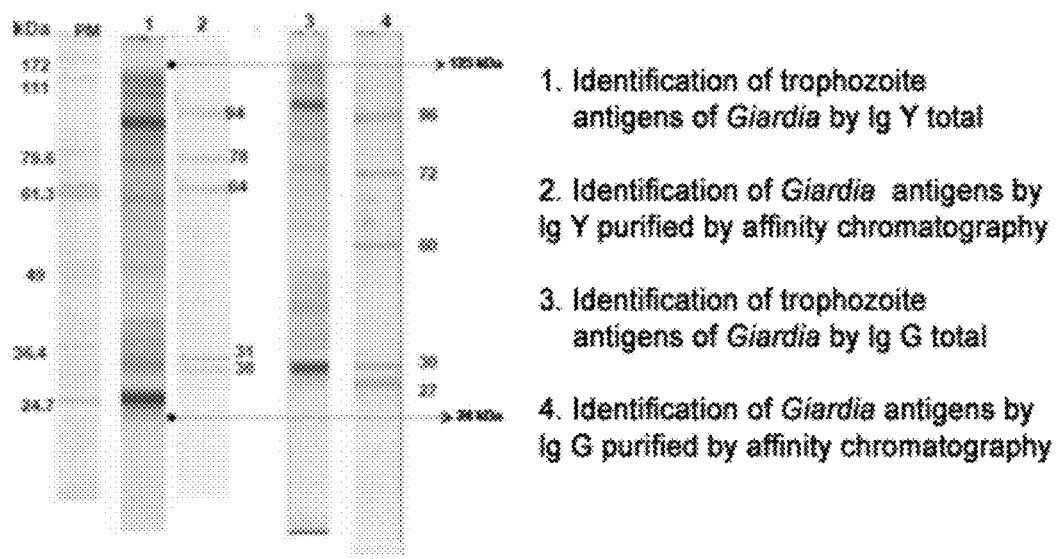
FIG. 12. Biological activity of polyclonal anti-*Giardia* IgG and anti-*Giardia* IgY antibodies purified by affinity chromatography and demonstrated by Western Blot.
Figure 13:
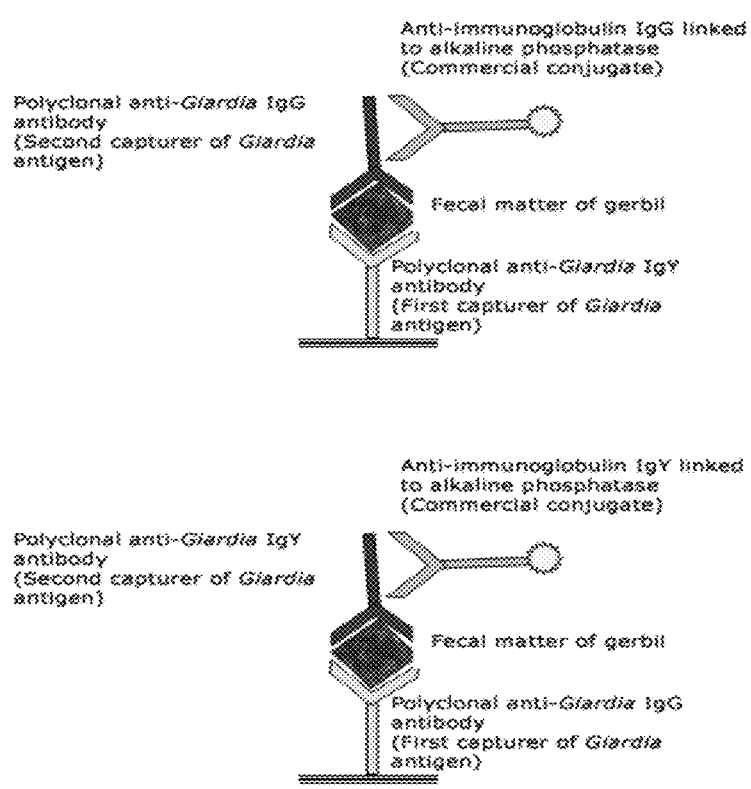
FIG. 13. Diagram of the detection of *Giardia* antigen by ELISA using polyclonal anti-*Giardia* IgG and IgY antibodies.

Determination of the Biological Activity of Polyclonal IgG Anti-*Giardia* Antibodies Developed in Rabbit and IgY Anti-*Giardia* Polyclonal Antibodies Developed in Hen Western Blot:

The biological activity of polyclonal anti-*Giardia* IgG antibodies developed in rabbit and IgY polyclonal antibodies anti-*Giardia* developed in hens, both independently purified by affinity chromatography, was demonstrated by the presence of bands indicating antigen binding (*Giardia* trophozoite) and antibody (polyclonal IgG anti-*Giardia* antibodies) or antigen binding (trophozoite of *Giardia*) and antibody (anti-*Giardia* IgY polyclonal antibodies) (FIG. 12).

*Giardia* trophozoite-specific antigens recognized by polyclonal IgG and IgY anti-*Giardia* antibodies by Western Blot ranged between 24 and 125 kDa and purified by affinity chromatography correspond to molecular weights of 94, 78, 64, 31 and 30 kDa and 86, 72, 60, 30 and 27 kDa, respectively.

Example 7. Indirect Sandwich ELISA for the Detection of Antigen of *Giardia* Using IgY Anti-*Giardia*, (First Capturer) and IgG Anti-*Giardia* (Second Capturer) Both Purified by Affinity Chromatography Anti-*Giardia* IgG and IgY polyclonal antibodies were purified by affinity chromatography using a *Giardia* total antigen column. The polyclonal IgY anti-*Giardia* is used directly in the ELISA as the first capture. The anti-*Giardia* IgG polyclonal antibody was re-purified using a matrix containing the three recombinant *Giardia* antigens and it acts as the second capturer and to which the rabbit anti-IgG-labeled alkaline phosphatase conjugate binds. The above allows greater sensitivity and specificity of ELISA in the detection of *Giardia* in fecal material eluates.

Standardization of Optimal Concentrations of Biologics for ELISA

Figure 14:
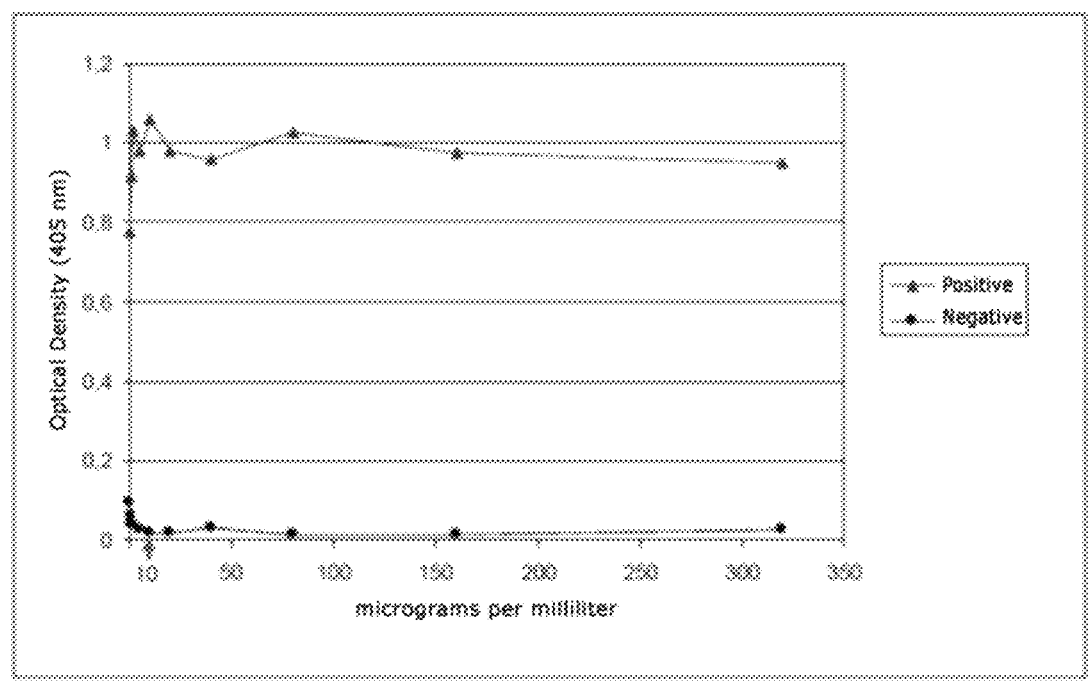
FIG. 14. Optimal dilution of polyclonal anti-*Giardia* antibodies.
Figure 15:
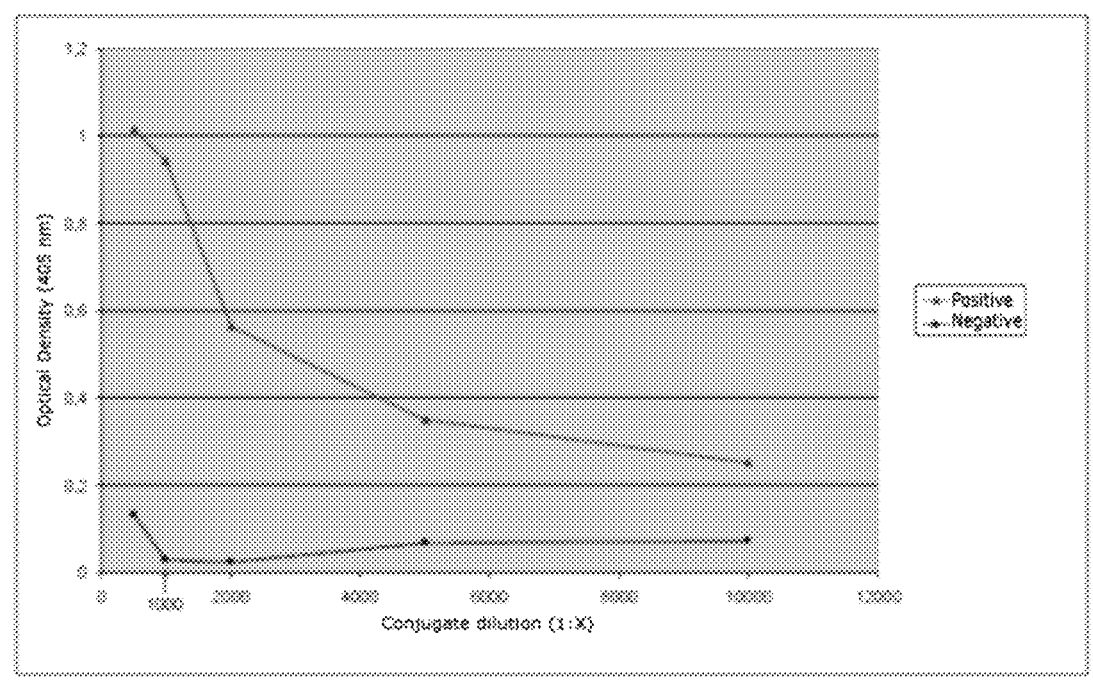
FIG. 15. Optimal dilution of rabbit anti-IgG conjugate bound to alkaline phosphatase.

The use of this scheme for the capture of parasite antigen in the feces eluates of the gerbil, allowed to establish optimal concentrations of polyclonal antibodies IgG anti-*Giardia* and IgY anti-*Giardia* of 10 µg/ml (FIG. 14) and a dilution of 1:1000 of rabbit anti-rabbit IgG conjugate to alkaline phosphatase (FIG. 15).

Diagnostic Discrimination

The parameters of the indirect sandwich ELISA for the detection of *Giardia* antigen in eluate of gerbil feces, animal model for studies of giardiasis using anti-*Giardia* IgY, (first capturer) and anti-*Giardia* IgG (second capturer) both purified by Affinity chromatography were: sensitivity (S): 100%, specificity (E): 100%, positive predictive value (PPV): 100% and negative predictive value (NPV): 100%.

These parameters are reliable, although in the course of infection, cysts of the parasite have not been observed in days 1, 2, 3, 4, 7, 8, 10, 11, 12, 13, 15, 16, 18, 19 and from day 21 to 30 post-infection and only constant presence of *Giardia* cysts during days 5, 6, 9, 14, 17 and 20 post-infection.

Figure 16:
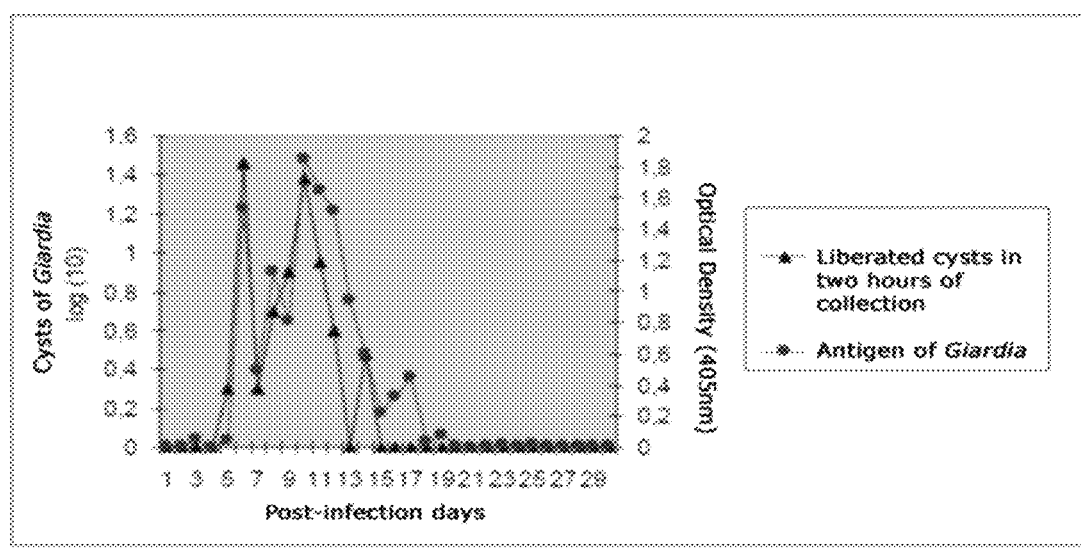
FIG. 16. Optical densities that indicate positivity in gerbils infected with the parasite from day zero of the infection until day 30 when the animals solve the infection themselves.
Figure 17:
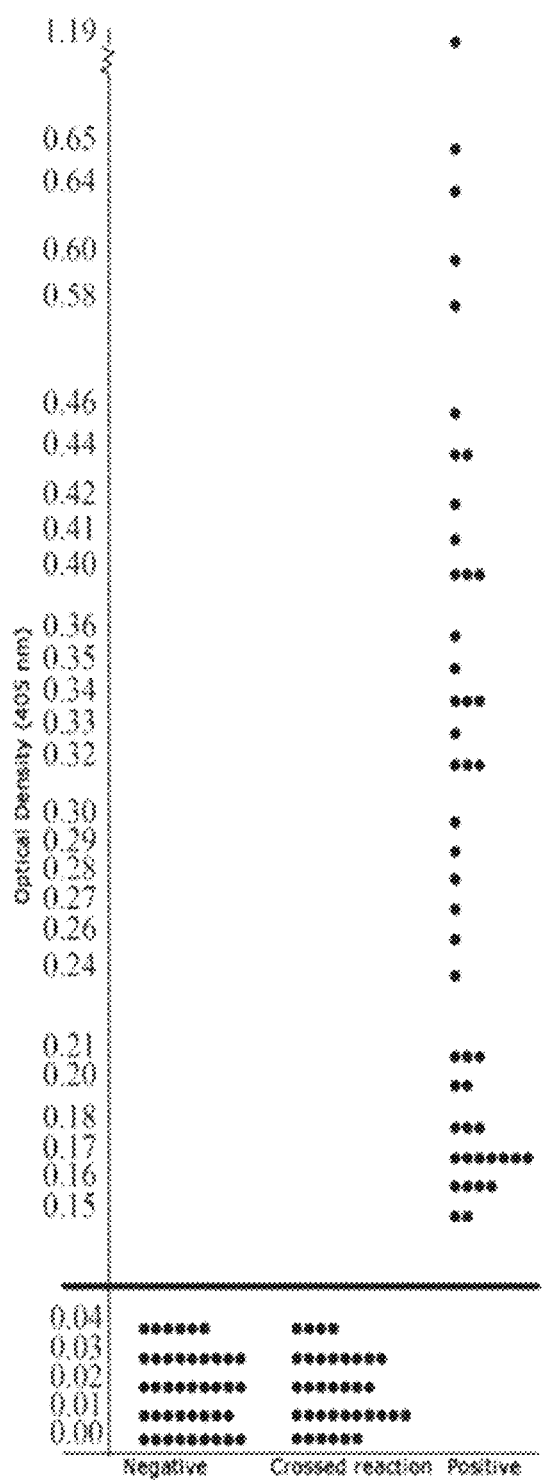
FIG. 17. Diagnostic discrimination of the indirect sandwich ELISA for the detection of *Giardia* antigen in human fecal eluate.

This is the natural phenomenon of intermittent cysts excretion, inherent in the biology of the parasite and independent of the host. Therefore, the optical densities that indicate positivity, although there is absence of cysts in the parasite, are reliable because it was known that feces came from gerbils infected with the parasite from day zero of the infection until day 30 when the animals resolve. by themselves the infection (FIG. 16).

Detection of *Giardia* Antigen in Human Fecal Eluates Using the Indirect Sandwich ELISA Developed to Detect *Giardia* Antigen in Animal Model Gerbil for Studies of Giardiasis.

Diagnostic Discrimination

The ELISA parameters for the detection of *Giardia* in eluates of human fecal matter using anti-*Giardia* IgY as the first capture and anti-*Giardia* IgG as the second capturer and both purified by affinity chromatography, were: sensitivity (S): 100%, specificity (E): 100%, positive predictive value (PPV): 100% and negative predictive value (NPV): 100%.

Example 8. Diagnostic Kit to Detect *Giardia* Antigens by the Dot-ELISA Methodology A dilution of 148 g/ml of polyclonal anti-cyst antibody and anti-trophozoite of *Giardia* in phosphate buffer (PBS) was performed. There was 1 µl of polyclonal antibody added to a circle of nitrocellulose membrane (MNC) of one centimeter in diameter.

It was incubated at 37° C. for 36 seconds for each sample of polyclonal antibody to be dried. Each MNC circle was blocked, individually, with 4% skimmed milk dissolved in PBS plus 1% Tween 20 (PBS-T) at 18° C. for one hour. The excess blocking solution was removed by inversion. 500 µl of each of the following samples were added, independently:

Fecal eluate without the presence of parasitologically diagnosed *Giardia* (negative control).

Eluate of fecal sample with the presence of parasitologically diagnosed *Giardia* (positive control).

Eluate of fecal matter to detect the presence of *Giardia* antigen or not.

The samples were incubated at 18° C. for 30 minutes. The fecal eluate was removed by inversion. There were 500 µl of PBS-T added to each MNC circle, individually. This was eliminated by inversion and the procedure was repeated five consecutive times.

There were 500 µl of anti-cyst polyclonal antibody and *Giardia* anti-trophozoite added at a concentration of 148 µg/ml PBS. It was incubated at 18° C. for 30 minutes. The polyclonal antibody was removed by inversion. There were 500 µl of PBS-T added to each MNC circle, individually. This was eliminated by inversion and the procedure was repeated five consecutive times. There were 500 µl of anti-rabbit IgG bound to alkaline phosphatase (conjugate) was added. It was incubated for 30 minutes. The conjugate was removed by inversion.

There were 500 µl of PBS-T was added to each MNC circle, individually. This was eliminated by inversion and the procedure was repeated four consecutive times. Each MNC circle was washed once with a phosphate buffer specific for the enzyme alkaline phosphatase (AP buffer). The AP solution was discarded by investment.

There were 50 µl of bromo-chloro-indolyl-phosphate, 50 µl of nitro-tetrazolium blue and 400 µl of AP solution were added. The development of the enzyme-substrate reaction was allowed at 18° C. for 10 minutes. The reaction was stopped with 500 µl of PBS plus 20 mM of EDTA.

Figure 18:
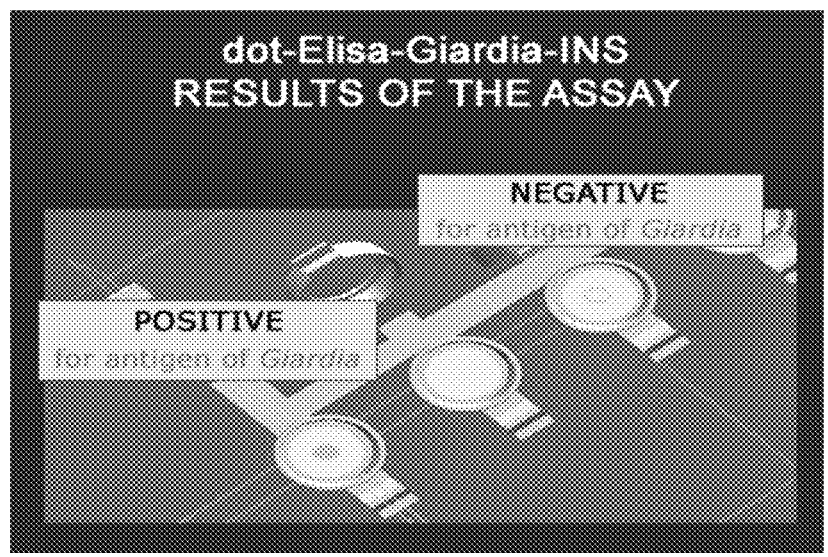
FIG. 18. Immunodiagnostic kit for the detection of fecal *Giardia*.

The purple reaction indicated the positive antigen-antibody binding reaction, and the absence of negative reaction color (FIG. 18).

The invention claimed is:

1. A kit for detecting *Giardia* antigens consisting of the following components: a first capture consisting of purified polyclonal anti-*Giardia* IgG or anti-*Giardia* IgY antibodies, and a second capture consisting of purified polyclonal anti-*Giardia* IgY or anti-*Giardia* IgG antibodies; provided that the first capture and the second capture are not the same; a solid matrix selected from polystyrene plates or nitrocellulose membrane (MNC); a blocking solution; phosphate buffer saline −0.1% Polysorbate 20 pH 7.2 (PBS-T); a conjugate of anti-IgY or anti-IgG antibodies bound to a reporter; and optionally a detection reagent; wherein if the second capture is a polyclonal anti-*Giardia* IgY antibody, the conjugate is a conjugate of anti-IgY; or wherein if the second capture is a polyclonal anti-*Giardia* IgG antibody, and the conjugate is a conjugate of anti-IgG; and wherein the purified polyclonal anti-*Giardia* IgG antibodies and the polyclonal anti-*Giardia* IgY antibodies are purified by affinity chromatography with the recombinant *Giardia* antigens Alpha Giardin 7.3, Kinesin 3 and Cyst wall protein 1 (CWP1).

2. The kit according to claim 1, wherein the reporter is an enzymatic, fluorescent, luminescent or chromophoric molecule.

3. The kit according to claim 1, wherein the blocking solution is 1% bovine serum albumin, or 4% skimmed milk dissolved in PBS plus 1% Polysorbate 20.

4. The kit according to claim 1, wherein the reporter is the enzyme alkaline phosphatase.

5. The kit according to claim 1, wherein the detection reagent is 5-bromo-4-chloro-3-indole phosphate (BCIP), nitrotetrazolium blue (NBT) or p-nitrophenylphosphate.

6. An in vitro test for the detection of *Giardia* antigens consisting of the following steps:
   adding a first capture on a solid matrix;
   incubating the solid matrix containing the first capture and washing with PBS-T;
   blocking using a blocking solution;
   incubating the solid matrix and removing the excess of blocking solution by inversion of the solid matrix or by washing with PBS-T;
   adding the sample on the solid matrix containing the first capture;
   incubating and removing the excess of sample by washing with PBS-T;
   adding a second capture;
   incubating and removing the excess of the second capture by inversion of the solid matrix or by washing with PBS-T;
   adding a conjugate of anti-IgY or anti-IgG antibodies bound to a reporter on the solid matrix;
   incubating and removing the excess of the conjugate by inversion or by washing with PBS-T; and optionally
   adding a detection reagent;
   wherein the first capture consists of purified polyclonal anti-*Giardia* IgG or anti-*Giardia* IgY antibodies, and the second capture consists of purified polyclonal anti-*Giardia* IgY or anti-*Giardia* IgG antibodies;
   provided that the first capture and the second capture are not the same;
   wherein if the second capture is a polyclonal anti-*Giardia* IgY antibody, the conjugate is a conjugate of anti-IgY; and
   wherein if the second capture is a polyclonal anti-*Giardia* IgG antibody, the conjugate is a conjugate of antiIgG; and
   wherein the purified polyclonal anti-*Giardia* IgG antibodies and the polyclonal anti-*Giardia* IgY antibodies are purified by affinity chromatography with the recombinant *Giardia* antigens Alpha Giardin 7.3, Kinesin 3 and Cyst wall protein 1 (CWP1).

* * * * *